US012728111B2

(12) United States Patent
Schopfer et al.

(10) Patent No.: US 12,728,111 B2
(45) Date of Patent: Sep. 8, 2026

(54) ELECTROPHILIC COMPOUNDS AND ELECTROPHILIC PRODRUGS FOR TREATING ANEURYSM

(71) Applicants: University of Pittsburgh—Of the Commonwealth System of Higher Education, Pittsburgh, PA (US); The Regents of the University of Michigan, Ann Arbor, MI (US)

(72) Inventors: Francisco J. Schopfer, Pittsburgh, PA (US); Bruce A. Freeman, Pittsburgh, PA (US); Yang Zhao, Ann Arbor, MI (US); Yuqing E. Chen, Superior Township, MI (US); Jifeng Zhang, Ann Arbor, MI (US)

(73) Assignees: University of Pittsburgh—Of the Commonwealth System of Higher Education, Pittsburgh, PA (US); The Regents of the University of Michigan, Ann Arbor, MI (US)

( * ) Notice: Subject to any disclaimer, the term of this patent is extended or adjusted under 35 U.S.C. 154(b) by 748 days.

(21) Appl. No.: 18/009,935

(22) PCT Filed: Apr. 20, 2021

(86) PCT No.: PCT/US2021/028175

§ 371 (c)(1),
(2) Date: Dec. 12, 2022

(87) PCT Pub. No.: WO2021/262298

PCT Pub. Date: Dec. 30, 2021

(65) Prior Publication Data

US 2023/0241019 A1 Aug. 3, 2023

Related U.S. Application Data

(60) Provisional application No. 63/042,707, filed on Jun. 23, 2020.

(51) Int. Cl.
*A61K 31/231* (2006.01)
*A61P 9/14* (2006.01)

(52) U.S. Cl.
CPC .............. *A61K 31/231* (2013.01); *A61P 9/14* (2018.01)

(58) Field of Classification Search
CPC .... A61K 31/04; A61K 31/194; A61K 31/201; A61K 31/22; A61K 31/231; A61P 43/00; A61P 9/00; A61P 9/14
See application file for complete search history.

(56) References Cited

U.S. PATENT DOCUMENTS 8,324,277 B2 12/2012 Freeman
9,066,902 B2 6/2015 Freeman et al.
10,213,417 B2 2/2019 Freeman et al.
10,744,106 B2 8/2020 Freeman et al.
10,751,310 B2 8/2020 Freeman et al.
10,765,652 B2 9/2020 Fazzari et al.
10,835,518 B2 11/2020 Freeman et al.
11,491,128 B2 11/2022 Fazzari et al.
2011/0039935 A1 2/2011 Pierzynowski
2014/0099354 A1 4/2014 Dietz et al.
2020/0101036 A1 4/2020 Ogawa et al.
2022/0040134 A1 2/2022 Freeman et al.

FOREIGN PATENT DOCUMENTS

WO WO 2005/073164 A1 8/2005
WO WO 2018/067709 4/2018
WO WO 2020/081957 A1 4/2020
WO WO 2021/188448 A1 9/2021
WO WO 2022/040222 A1 2/2022

OTHER PUBLICATIONS

Cleveland Clinic, https://my.clevelandclinic.org/health/diseases/22769-aneurysm, 2022 (Year: 2022).*
Nettersheim et al., Cardiovasc Res. Jul. 20, 2022;118(9) :2211-2225 (Year: 2022).*
Zhao, Cardiovasc Drugs Ther. Jul. 15, 2021;35(5):939-951 (Year: 2021).*
Ambrozova, Biochimica et Biophysica Acta, 2016 (Year: 2016).*
ROM, Curr Opin Lipidol 2020 (Year: 2020).*
Yanbo, National Institutes of Health, 2020 (Year: 2020).*
Shen (Year: 2014) -Interv Neuroradiol. Jul.-Aug. 2014;20(4):442-7.*
Gao (Year: 2023), Signal transduction and Targeted Therapy, 2023.*
Wang et al. (Scientific Reports vol. 4, Article No. 4905, 2014) (Year: 2014).*
Tousoulis (International Journal of Cardiology, vol. 165, Issue 2, May 10, 2013, 213-216). (Year: 2013).*
International Search Report and Written Opinion issued for International Application No. PCT/US2021/028175 on Aug. 11, 2021.
Office Action issued in Japanese Patent Application No. 2022-579739, dated Apr. 11, 2025, English Translation.
Robledinos-Anton et al., "Activators and Inhibitors of NRF2: A Review of Their Potential Clinical Development," *Oxidative Medicine and Cellular Longevity*, vol. 2019, 20 pages.

(Continued)

*Primary Examiner* — Umamaheswari Ramachandran
(74) *Attorney, Agent, or Firm* — Klarquist Sparkman, LLP

(57) ABSTRACT

A method comprising administering to a subject having an aneurysm, suspected of having an aneurysm, or at risk of developing an aneurysm, a therapeutically effective amount of a compound selected from (i) a nitroalkene fatty acid, (ii) an unsaturated fatty acid having an electron withdrawing group, a leaving group, and a carbon-carbon double bond disposed between the electron withdrawing group and the leaving group, (iii) a thiolated nitro fatty acid, (iv) a dicarboxylic acid compound containing an electron withdrawing group, or a mixture of at least two of (i)-(iv).

7 Claims, 12 Drawing Sheets

(56) References Cited

OTHER PUBLICATIONS

Shi et al., "Nrf-2 signaling inhibits intracranial aneurysm formation and progression by modulating vascular smooth muscle cell phenotype and function," *Journal of Neuroinflammation*, 16:185, 2019.
Cui et al., "Nitrated Fatty Acids: Endogenous Anti-inflammatory Signaling Mediators," *Journal of Biological Chemistry*, vol. 281, No. 47, pp. 35686-35698, Nov. 24, 2006.
Extended European Search Report for European Application No. 21828888.4, dated Jun. 10, 2024, 13 pages.
Zhao et al., "Suppression of Vascular Macrophage Activation by Nitro-Oleic Acid and its Implication for Abdominal Aortic Aneurysm Therapy," *Cardiovascular Drugs and Therapy*, 35: 939-951 (2021).
Final Office Action, dated Dec. 15, 2025, issued in corresponding Japan Application No. 2022-579739. 3 pages.

* cited by examiner oxLDL (50µg/mL)
-
+
Ct
OA
$NO_2$-OA
P65 (65 kDa)
Lamin A/C (74/63 kDa)
GAPDH (37 kDa)
Nuclear Cytosolic p=0.0238
Normalized P65 nuclear to cytosolic ratio
0
10
20
30
40
50
Vehicle
OA
OA-$NO_2$
oxLDL
oxLDL+OA
oxLDL+$NO_2$-OA FIG. 3F
TNF α concentration (pg/mL)
p=0.3290
Vehicle
OA
$NO_2$-OA
oxLDL
oxLDL+OA
oxLDL+$NO_2$-OA
FIG. 3E
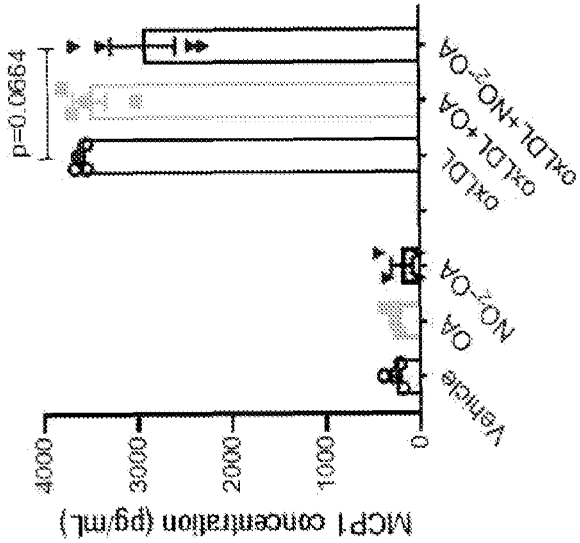
FIG. 3D
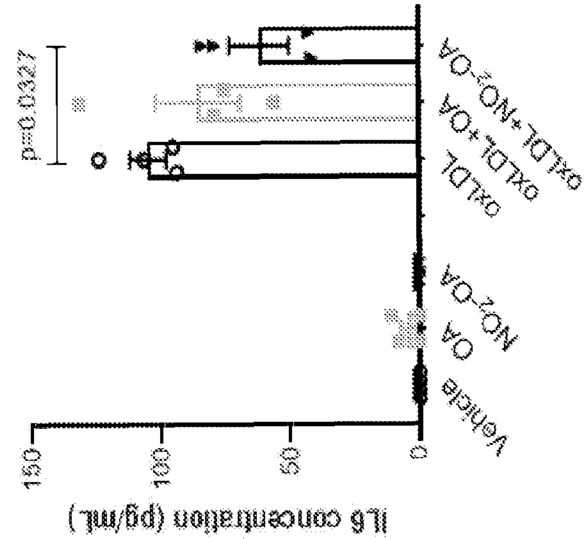

| | Vehicle | OA | $NO_2$-OA |
|---|---|---|---|
| EC50 | 1.095e-010 | 2.290e-010 | 1.212e-009 |

| | Vehicle | OA | $NO_2$-OA |
|---|---|---|---|
| EC50 | 9.322e-011 | 3.746e-010 | 7.243e-010 |

FIG. 4B $NO_2$-OA ($IC_{50}$) = 2.8μM

ELECTROPHILIC COMPOUNDS AND ELECTROPHILIC PRODRUGS FOR TREATING ANEURYSM

CROSS REFERENCE TO RELATED APPLICATIONS

This application is the U.S. National Stage of International Application No. PCT/US2021/028175, filed Apr. 20, 2021, which was published in English under PCT Article 21(2), which in turn claims the benefit of U.S. Provisional Application No. 63/042,707, filed Jun. 23, 2020, which is incorporated by reference herein in its entirety.

ACKNOWLEDGMENT OF GOVERNMENT SUPPORT

This invention was made with government support under grant numbers HL068878; HL138139; HL064937; DK112854; GM125944; HL132550; and HL103455 awarded by the National Institutes of Health. The government has certain rights in the invention.

BACKGROUND

Characterized by the enlargement of the abdominal aorta over its standard size (≥30 mm or 1.5 times), abdominal aortic aneurysm (AAA) is a primary medical concern owing to its wide prevalence, high mortality rate and lack of effective treatment. Despite the success achieved in reducing the AAA-related mortality rate through preventive screening in high-risk men between 65 to 75 years, open and endovascular surgeries are still the only treatments available, with just a small proportion of AAA patients eligible for surgical repair. Besides, patients undergoing either surgery are not risk-free. While open repair is associated with a relatively high risk of perioperative mortality, the widely used endovascular repair nowadays also increases the likelihood of postsurgical leaking, leaving an urgent need for alternative therapeutic strategies. Although vascular inflammation, macrophage infiltration, oxidative stress, and extracellular matrix degradation are widely accepted as the pathological features of AAA, their direct causative roles and contribution to both progression and to late stage disease outcomes are not well-defined. While several pharmacologic agents targeting certain individual facets of AAA appeared to be promising in preclinical studies, leverage into beneficial outcomes in clinical settings of AAA is not evident to date, likely due to the complex pathophysiological nature of AAA.

SUMMARY

Disclosed herein is a method comprising administering to a subject having an aneurysm, suspected of having an aneurysm, or at risk of developing an aneurysm, a therapeutically effective amount of a compound selected from (i) a nitroalkene fatty acid, (ii) an unsaturated fatty acid having an electron withdrawing group, a leaving group, and a carbon-carbon double bond disposed between the electron withdrawing group and the leaving group, (iii) a thiolated nitro fatty acid, (iv) a dicarboxylic acid compound containing an electron withdrawing group on a double bond that induces electrophilic character, or a mixture of at least two of (i)-(iv).

The foregoing will become more apparent from the following detailed description, which proceeds with reference to the accompanying figures.

DETAILED DESCRIPTION

Terminology

Figure 1B:
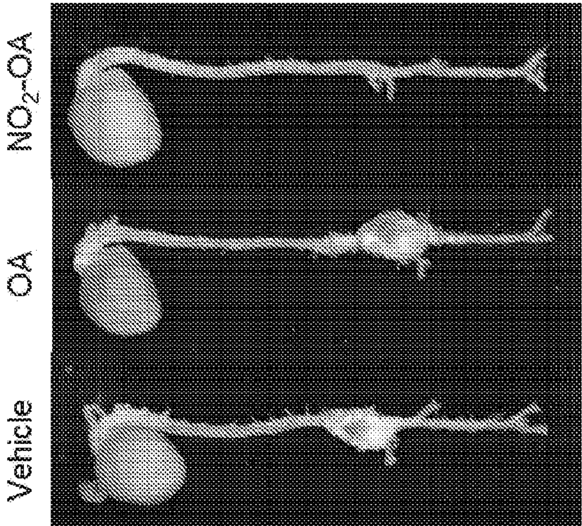
FIG. 1. Characterization of the protective effect of $NO_2$—OA (10-nitro-octadec-9-enoic acid) in the Ang II plus hypercholesterolemia-induced AAA mouse model. (A) Schematic illustration of the in vivo experimental design. Ten week old male C57BL/6 mice were IP injected with AAV carrying PCSK9 gain-of-function (D377Y) mutation and fed a western diet. After two weeks, each mouse was implanted with a pump delivering AngII at a rate of 1,500 ng/kg/min plus an additional pump containing either PEG-400 (vehicle), OA or $NO_2$—OA with a delivery rate of 5 mg/kg/day (n=25 to 30 per group) and carried to the endpoint for another four weeks. Mice with ruptured aorta within the first week or with total plasma cholesterol less than 250 mg/dl were excluded from the study. (B) Representative morphological differences of the abdominal aorta. (C) AAA incidence calculated by using 1.2 mm as the cutoff diameter indicated by the dotted line in (D). (D) Average maximal diameter of the suprarenal aorta region. (E) Representative H&E and VVG staining of the paraffin-embedded suprarenal aortic cross-sections (5 μm). (F) Grade of elastic fiber degradation in the aorta (1 to 4). A 2×3 Fisher's exact test followed by posthoc test was performed for (C). For (D) and (F), the Kruskal-Wallis test followed by Dunn's multiple comparisons was performed. Continuous data are presented as mean±SEM. Scale bar=20 μm for (E). A $p<0.05$ for both the main test and post hoc test was considered statistically significant.

The following explanations of terms and methods are provided to better describe the present compounds, compositions and methods, and to guide those of ordinary skill in the art in the practice of the present disclosure. It is also to be understood that the terminology used in the disclosure is for describing particular embodiments and examples only and is not intended to be limiting.

"Administration" as used herein is inclusive of administration by another person to the subject or self-administration by the subject.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkyl" refers to a branched or unbranched saturated hydrocarbon group, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and one or more triple bonds. Alkynyl groups may be unsubstituted or substituted.

The term "amine" or "amino" refers to a group of the formula —NRR', where R and R' can be, independently, hydrogen or an alkyl, alkenyl, alkynyl, acyl, aryl, aralkyl, cycloalkyl, halogenated alkyl, or heterocycloalkyl group. For example, an "alkylamino" or "alkylated amino" refers to —NRR', wherein at least one of R or R' is an alkyl. A suitable amine or amino group is acetamido An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

As used herein, "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, OH, alkoxy, amino, $CO_2H$, $CO_2$alkyl, aryl, and heteroaryl. Exemplary aryl groups include but are not limited to phenyl, naphthyl, tetrahydronaphthyl, chlorophenyl, methylphenyl, methoxyphenyl, trifluoromethylphenyl, nitrophenyl, and 2,4-methoxychlorophenyl.

The term "biological sample" refers to tissue, cells, cellular extract, or homogenized tissue extract.

The term "co-administration" or "co-administering" refers to administration of a compound disclosed herein with at least one other therapeutic agent or therapy within the same general time period, and does not require administration at the same exact moment in time (although co-administration is inclusive of administering at the same exact moment in time). Thus, co-administration may be on the same day or on different days, or in the same week or in different weeks. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent and/or lowers the frequency of administering the potentially harmful (e.g., toxic) agent. "Co-administration" or "co-administering" encompass administration of two or more active agents to a subject so that both the active agents and/or their metabolites are present in the subject at the same time. Co-administration includes simultaneous administration in separate compositions, administration at different times in separate compositions, or administration in a composition in which two or more active agents are present. Co-administration also encompasses delivery of a first agent via a first administration route and delivery of a second agent via a second administration route, wherein the first administration route and the second administration route are the same (e.g., both oral) or different (e.g., first is oral, second is topical).

The term "derivative" refers to a compound that is derived from a similar compound, or a compound that can be imagined to arise from another compound, if one or more atoms are replaced with another atom or group of atoms.

The term "haloalkyl," refers to a $C_1$-$C_8$ alkyl group wherein one or more hydrogen atoms in the $C_1$-$C_8$ alkyl group is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "halogen" and "halo" refers to —F, —Cl, —Br or —I.

The term "heteroatom" is meant to include oxygen (O), nitrogen (N), and sulfur (S). The term "heteroaryl" is employed here to refer to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and preferably one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "heterocycle" refers to a monocyclic, bicyclic, tricyclic, or polycyclic systems, which are either unsaturated or aromatic and which contains from 1 to 4 heteroatoms, independently selected from nitrogen, oxygen and sulfur, wherein the nitrogen and sulfur heteroatoms are optionally oxidized and the nitrogen heteroatom optionally quatemized, including bicyclic, and tricyclic ring systems. The heterocycle may be attached via any heteroatom or carbon atom. Heterocycles include heteroaryls as defined above. Representative examples of heterocycles include, but are not limited to, benzoxazolyl, benzisoxazolyl, benzthiazolyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents.

"Heterocycloalkyl" denotes to a monocyclic or bicyclic ring system containing one or two saturated or unsaturated rings and containing at least one nitrogen, oxygen, or sulfur atom in the ring. The term "cycloalkyl" refers to a monocyclic or bicyclic ring system containing one or two saturated or unsaturated rings.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, $—CH_2OH$, $—CH_2CH_2OH$, $—CH_2CH_2CH_2OH$, $—CH_2CH_2CH_2CH_2OH$, $—CH_2CH_2CH_2CH_2CH_2OH$, $—CH_2CH_2CH_2CH_2CH_2CH_2OH$, and branched versions thereof.

The term "oxo" refers to a ═O atom attached to a saturated or unsaturated ($C_3$-$C_8$) cyclic or a ($C_1$-$C_8$) acyclic moiety. The ═O atom can be attached to a carbon, sulfur, and nitrogen atom that is part of the cyclic or acyclic moiety.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, PA (19th Edition).

The compounds of the invention can exist in various isomeric forms, including configurational, geometric, and conformational isomers, as well as existing in various tautomeric forms, particularly those that differ in the point of attachment of a hydrogen atom. The term "isomer" is intended to encompass all isomeric forms of a compound of this invention, including tautomeric forms of the compound.

Particular examples of the presently disclosed compounds may include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The presently disclosed compounds can have at least one asymmetric center or geometric center, cis-trans center (C═C, C═N). All chiral, diasteromeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}F$, etc.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by BURGER'S MEDICINAL CHEMISTRY AND DRUG DISCOVERY 6th ed. (Wiley, 2001) and DESIGN AND APPLICATION OF PRODRUGS (Harwood Academic Publishers Gmbh, 1985).

Overview

In one embodiment disclosed herein, there is provided a method for treating an aneurysm in a subject that includes administering to the subject a therapeutically effective amount of a compound selected from (i) a nitroalkene fatty acid, (ii) an unsaturated fatty acid having an electron withdrawing group, a leaving group, and a carbon-carbon double bond disposed between the electron withdrawing group and the leaving group, (iii) a thiolated nitro fatty acid, (iv) a dicarboxylic acid compound containing an electron withdrawing group on a double bond that induces an electrophilic character, or a mixture thereof. The aneurysm may be an aortic aneurysm or a vascular aneurysm (such as arterial aneurysm). In certain embodiments the aortic aneurysm may be an abdominal aortic aneurysm (AAA). In certain embodiments the aortic aneurysm may be a thoracic aortic aneurysm (TAA). In certain embodiments the aortic aneurysm may be a thoracoabdominal aortic aneurysm (TAAA). Other illustrative aneurysms include intracranial aneurysm, aneurysms of celiac artery, mesenteric artery, renal arteries, splenic artery, hepatic artery, iliac arteries, femoral artery, popliteal artery and any branches of the aorta.

Nitro-fatty acids represent a convergence between unsaturated fatty acid, nitrogen oxide and electrophile-mediated signaling, acting via pleiotropic mechanisms as inflammatory and metabolic regulators in model systems and humans. Nanomolar concentrations of nitro-fatty acids can form endogenously in response to nitric oxide- and nitrite-derived nitrogen dioxide generated via local inflammatory and oxidative reactions, as well as in the gastrointestinal tract where low pH favors fatty acid nitration. While nitro-fatty acids participate in reversible Michael addition reactions with cellular nucleophiles, most biological activity is mediated by the post-translational modification of critical cysteines found in regulatory proteins. For instance, nitro-fatty acids activate PPARγ, inhibit p65-dependent nuclear factor-kappa B (NF-kB) activation, induce the heat shock response, and promote nuclear factor erythroid 2-related factor 2 (Nrf2) dependent anti-oxidative effect. Additionally, the pharmacodynamics and pharmacokinetic characteristics of a Phase 1 human study of CXA-10 (10-nitro-oleic acid, also referred to herein as $NO_2$—OA) showed that CXA-10 is safe within a therapeutic window (25-450 mg/day) and attenuated systemic inflammation in human volunteers. This was reflected by decreased circulating monocyte chemoattractant protein 1 (MCP1) and interleukin 6 (IL6) levels. In parallel, in vivo studies administering nitro-fatty acids via either oral or non-oral routes in various animal models, demonstrated the protective effect of nitro-fatty acids in multiple disease models including atherosclerosis, hypertension, vascular inflammation, cardiac ischemia/reperfusion injury, kidney nephropathy and non-alcoholic fatty liver disease.

The transport mechanism of nitro-fatty acids provides a distinct and specific distribution to cells and organs, defining target tissues and cell signaling events. For instance, nitro-fatty acids in the systemic circulation are esterified to triglycerides (TG). They can be taken up, after hydrolysis, by circulating monocytes, vascular endothelium and macrophages (e.g., through CD36, FABPs) to exert intracellular signaling activities. In this regard, a monocyte-vascular-macrophage axis may play a predominant role in the nitro-fatty acid-mediated beneficial vascular effects. This is supported by the observation that the administration of CXA-10 in humans induces Nrf2-regulated genes and heat shock response in peripheral blood mononuclear cells. The fact that nitro-fatty acids decrease differentiation of monocytes to macrophages induced by colony-stimulating factors, inhibit LPS induced leukocyte adhesion to the vascular endothelium, and prevent pro-inflammatory macrophage polarization, further point to the importance of nitro-fatty acids in regulating monocyte/macrophage biology.

In spite of urgent unmet need for effective pharmaceutical management of AAA, recent clinical trials of AAA therapies using small molecule drug candidates targeting individual factors like blood pressure, plasma cholesterol level, vascular inflammation and ECM degradation failed to provide a satisfying outcome. At the same time, multiple studies and clinical trials have demonstrated the participation and active contribution of monocytes/macrophages to all stages of AAA development, involving distinct mechanisms that mediate the recruitment of immune cells, activation of pro/anti-inflammatory responses and degradation of the aortic wall. Nitro-fatty acids, endogenous mediators of diverse inflammatory and metabolic cell signaling and gene expression responses, have displayed various beneficial effects in vascular disease and monocytes/macrophages activation. CXA-10, a synthetic homolog of one specific regioisomer of $NO_2$—OA, is presently being studied in phase II clinical trials for treating a chronic inflammatory-related renal disorder (focal segmental glomerulosclerosis) and pulmonary arterial hypertension (NCT04053543, NCT03422510).

Disclosed herein are the protective effects of $NO_2$—OA in a mouse model of AAA induced by Angiotensin II (AngII) and hypercholesterolemia and identified significantly decreased leukocyte infiltration into the vascular wall. Using oxidized low-density lipoprotein (oxLDL) and AngII, we recapitulated the anti-inflammatory function of $NO_2$—OA and showed that it could be partially accounted for by enhanced PPARγ gamma signaling and decreased p65-dependent NFκB activity in cultured RAW264.7 cells and primary bone marrow-derived macrophages (BMDMs). Additionally, we report the biased-regulation of $NO_2$—OA on macrophage prostaglandin E2 (PGE2)-induced activation of the prostaglandin E2 receptor 4 (EP4), a pathway previously associated with human aneurysm development.

It is disclosed herein that $NO_2$—OA in an AngII/PCSK9-induced AAA mouse model attenuates AAA formation. The pathological assessment uncovered a significantly suppressed suprarenal aneurysm enlargement and less elastin degradation (FIG. 1), highlighting the protective role of $NO_2$—OA and other electrophilic fatty acids in AAA development.

Vascular infiltration by leukocytes and macrophages, an essential feature and contributor to AAA development, was significantly downregulated by $NO_2$—OA. This effect is possibly due to the simultaneous downregulation of adhesion molecules expression and chemo attractant secretion (FIG. 2). Furthermore, in vitro studies using biologically relevant stimuli demonstrated a protective role of $NO_2$—OA, including reduced migration of macrophages upon AngII-induced endothelial stimulation. Moreover, potent inhibition of oxLDL-induced NFκB activation and nuclear translocation of the p65 transcription factor with $NO_2$—OA treatment was observed. This effect was mediated, at least partially, by the activation of PPARγ and inhibited by the irreversible PPARγ inhibitor GW9662 (FIG. 3).

Figure 4A:
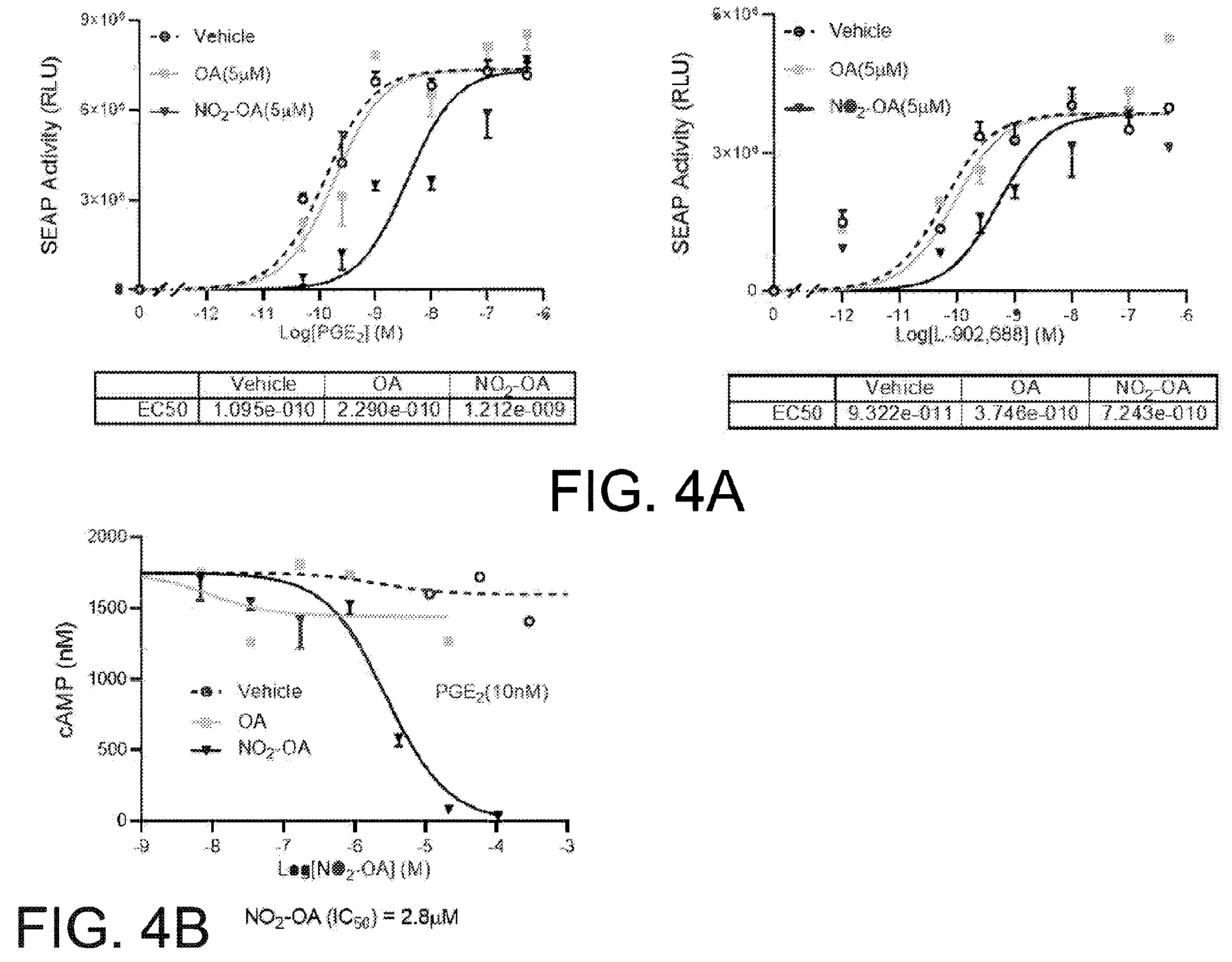
FIG. 4. $NO_2$—OA inhibits PGE2-dependent EP4 cAMP downstream signaling. (A) Three parameters nonlinear regression of EP4 global fitting dose-response curve. The SEAP-EP4 reporter was overexpressed in 293T cells and the $NO_2$—OA induced EC50 shift was calculated using PGE2 as an agonist. (B) HTRF assay of cAMP-Gs coupled receptor. Inhibition of PGE2-induced cAMP recruitment (at IC90 10 nM) by various doses of NO2-OA in 293T cells overexpressing EP4. (C) Modeling of the predicted binding site of NO2-OA and PGE2 to the EP4 receptor with the highest rank score. (D) Representative figure of gelatin zymography indicating MMP 2/9 activity. BMDMs were incubated with L-902,688 (100 nM) plus vehicle, OA (2.5 μM) or $NO_2$—OA (2.5 μM) for 12 h, and MMP 2&9 activity was measured by gelatin zymography. For (A) and (B), three or four parameters, global or separate fitting, constraints, and the significance of EC50 were determined in Prism. Data presented as mean±SEM. A $p<0.05$ was considered statistically significant.

Representing a convergence of lipophilic and electrophilic chemical structures, $NO_2$—FAs not only function on intracellular nuclear receptors but also modulate membrane-associated proteins such as Toll-like receptors. Herein, we also reveal the inhibition of PGE2-induced EP4 activation by $NO_2$—OA (FIG. 4). It is widely accepted that the macrophage COX2-PGE2-EP4 axis participates in the etiology of human AAA disease. Studies using different EP4-specific antagonists have demonstrated protection against AngII/ApoE−/−, as well as CaCl2)-induced AAA formation in mice, with decreased MMP production and activity as common features. However, EP4 deficiency in bone marrow-derived cells was found to increase inflammation and AAA incidence. These conflicting observations could be a consequence of differential effects on the downstream signaling pathways since the Gs-coupled EP4 not only facilitates cAMP recruitment but also counteracts NFkB activation through the formation of EPRAP/p105 complex. In this regard, we demonstrated that $NO_2$—OA functions as a biased regulator of EP4 signaling responses by increasing the EP4-dependent anti-inflammatory effects of PGE2 induced by inflammatory stimuli without interfering with the EPRAP/p105 interaction.

Figure 5:
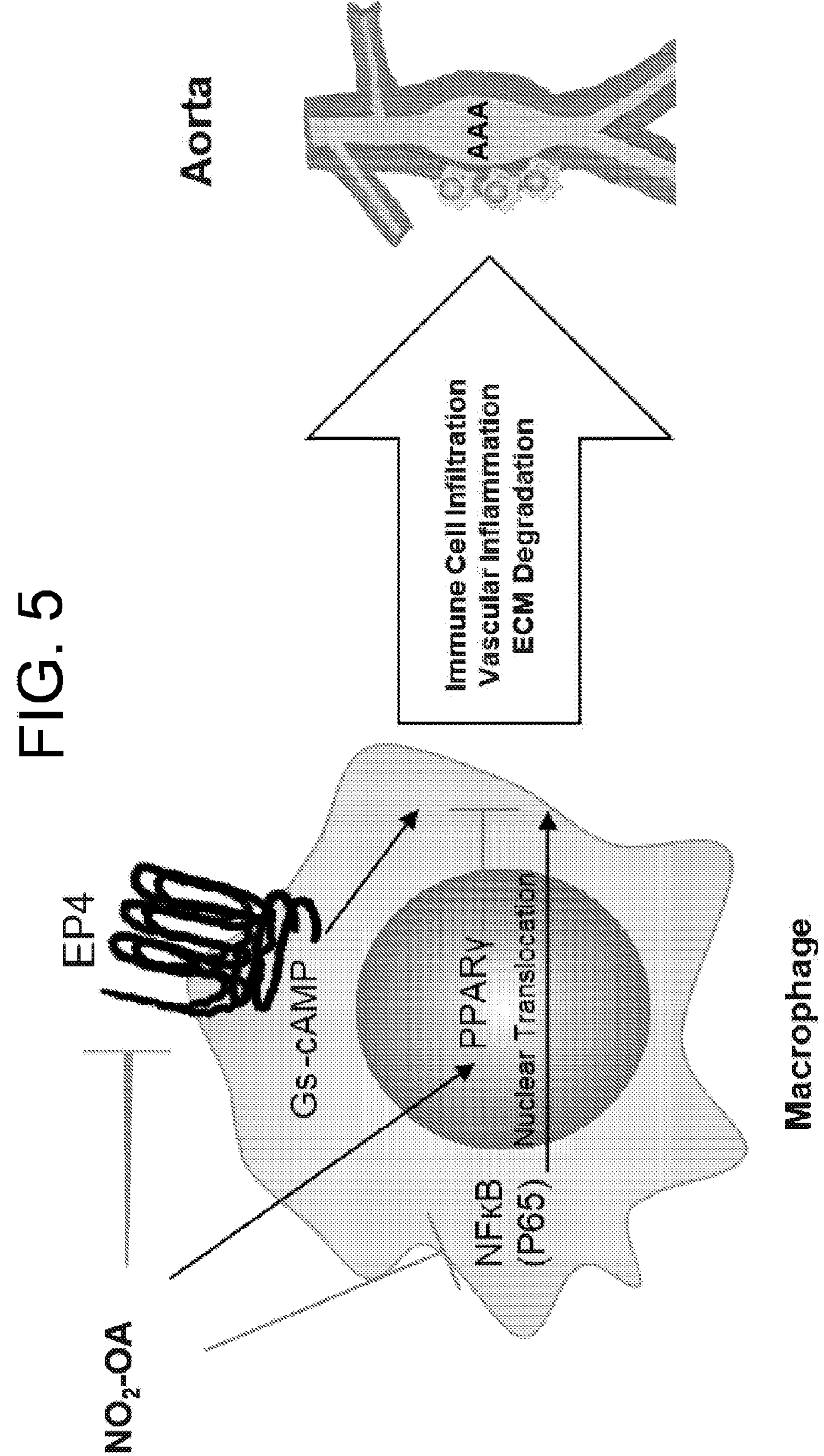
FIG. 5. Graphical summary of the study.

Revealed herein is a demonstration of the protective effect of electrophilic $NO_2$—FAs against macrophage activation and AAA development (FIG. 5). Our results underscore a potential new clinical therapeutic opportunity for nitro-fatty acids, such as the nitroalkene derivatives of oleic acid used herein, in the treatment of AAA. In addition, our findings provide a rationale for using multi-targeted, pleiotropic electrophilic compounds to treat this pathogenically-diverse and complex disease.

Compound (i)—Nitroalkene Fatty Acid

In certain embodiments, the (i) nitroalkene fatty acid is a compound that includes at least one carbon-carbon double bond and at least one nitro group. Certain nitroalkene fatty acids are described, for example, in U.S. Pat. No. 7,776,916.

One illustrative embodiment of a nitroalkene is a structure of formula I:

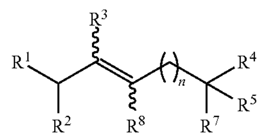

wherein $R^1$ is hydrogen, $C_1$-$C_{24}$ alkyl, $C_1$-$C_{24}$ alkenyl, or $C_1$-$C_{24}$ alkynyl;

$R^2$, $R^3$, $R^7$, and $R^8$ are each independently, hydrogen, oxygen, $C_1$-$C_{24}$ alkyl, $NO_2$, OH, or OOH;

$R^4$ is a terminal $COOR^6$ group, wherein $R^6$ is hydrogen, or a $C_1$-$C_{24}$ alkyl;

$R^5$ is hydrogen, $C_1$-$C_{24}$ alkyl, or $R^4$ and $R^5$ collectively form $=C(R^9)(R^{10})$, wherein $R^9$ comprises $C_1$-$C_{24}$ alkyl, $C_1$-$C_{24}$ alkenyl, or $C_1$-$C_{24}$ alkynyl, or wherein $R^9$ is a terminal $COOR^6$ group, and $R^{10}$ is hydrogen, $NO_2$, OH, or OOH;

n is from 1 to 24; and wherein the nitroalkene fatty acid includes at least one $NO_2$ group.

In certain embodiments of formula I, $R^1$ is $C_1$-$C_{24}$ alkyl, more particularly $C_3$-$C_{20}$ alkyl.

In certain embodiments of formula I, $R^2$ is hydrogen.

In certain embodiments of formula I, one of $R^3$ or $R^8$ is $NO_2$ and the other of $R^3$ or $R^8$ is hydrogen.

In certain embodiments of formula I, n is 3 to 20.

In certain embodiments of formula I, $R^4$ is —COOH.

In certain embodiments of formula I, $R^5$ is hydrogen.

In certain embodiments of formula I, $R^7$ is hydrogen.

In certain embodiments of formula I, $R^4$ is —COOH; $R^5$ is methyl; and $R^7$ is methyl.

In certain embodiments of formula I, $R^1$ is $C_1$-$C_{24}$ alkyl, more particularly $C_3$-$C_{20}$ alkyl; $R^2$ hydrogen; one of $R^3$ or $R^8$ is $NO_2$ and the other of $R^3$ or $R^8$ is hydrogen; $R^4$ is —COOH; $R^5$ is hydrogen; and $R^7$ is hydrogen.

Another illustrative embodiment of a nitroalkene is a structure of formula II:

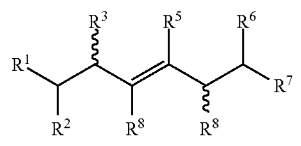

wherein $R^1$ is hydrogen, $C_1$-$C_{24}$ alkyl, $C_1$-$C_{24}$ alkenyl, or $C_1$-$C_{24}$ alkynyl;

$R^2$, $R^4$, $R^5$ and $R^6$ are each hydrogen;

$R^7$ is a terminal $COOR^9$ group, wherein $R^9$ is hydrogen or a $C_1$-$C_{24}$ alkyl; and $R^3$ and $R^8$ are each independently, hydrogen, oxygen, $C_1$-$C_{24}$ alkyl, $NO_2$, OH, $ONO_2$, NO, ONO or OOH, provided at least one of $R^3$ or $R^8$ is $NO_2$ and the other of $R^3$ or $R^8$ is hydrogen, ONO or $ONO_2$.

In certain embodiments of formula II, $R^1$ is $C_1$-$C_{24}$ alkyl, more particularly $C_3$-$C_{20}$ alkyl; $R^9$ is hydrogen; and $R^3$ is $NO_2$ and $R^8$ is $ONO_2$ or $R^8$ is $NO_2$ and $R^3$ is $ONO_2$.

An additional illustrative embodiment of another nitro group-containing compound is a structure of formula III:

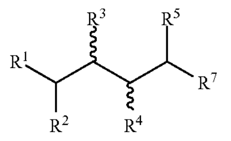

wherein $R^1$ is hydrogen, $C_1$-$C_{24}$ alkyl, $C_1$-$C_{24}$ alkenyl, or $C_1$-$C_{24}$ alkynyl;

$R^2$ and $R^5$ are each hydrogen;

$R^7$ is a terminal $COOR^6$ group, wherein $R^6$ is hydrogen or a $C_1$-$C_{24}$ alkyl; and $R^3$ and $R^4$ are each independently, hydrogen, oxygen, $C_1$-$C_{24}$ alkyl, $NO_2$, OH, $ONO_2$, NO, ONO or OOH, provided at least one of $R^3$ or $R^4$ is $NO_2$ and the other of $R^3$ or $R^4$ is hydrogen, ONO or $ONO_2$.

In certain embodiments of formula III, $R^1$ is $C_1$-$C_{24}$ alkyl, more particularly $C_3$-$C_{20}$ alkyl; $R^6$ is hydrogen; $R^3$ is $NO_2$ and $R^4$ is $ONO_2$ or $R^4$ is $NO_2$ and $R^3$ is $ONO_2$.

In certain embodiments, the nitroalkene fatty acid is 10-nitro-octadec-9-enoic acid (referred to herein as "$NO_2$—OA").

In certain embodiments, the nitroalkene fatty acid is 9-nitro-octadec-9-enoic acid.

In certain embodiments, the nitroalkene fatty acid is 8-nitro-nonadec-9-enoic acid.

In certain embodiments, the nitroalkene fatty acid is 7-$NO_2$-nonadec-7-enoic acid.

In certain embodiments, the nitroalkene fatty acid is 5-$NO_2$-eicos-5-enoic acid or 6-$NO_2$-eicos-5-enoic acid.

In certain embodiments, the nitroalkene fatty acid is 9-nitrooctadeca-9,11-dienoic acid In certain embodiments, the nitroalkene fatty acid is 12-nitrooctadeca-9,11-dienoic acid In certain embodiments, the nitroalkene fatty acid is 9-nitro-12-(nitrooxy)octadec-10-enoic acid.

In certain embodiments, the nitroalkene fatty acid is 12-nitro-9-(nitrooxy)octadec-10-enoic acid.

In certain embodiments, the nitroalkene is substantially pure. In this aspect, the stereochemistry about the carbon-carbon double bond is substantially cis (or Z) or substantially trans (or E).

In certain embodiments, the nitroalkene fatty acid has a Z configuration.

Compound (ii)—Unsaturated Fatty Acid Having an Electron Withdrawing Group, a Leaving Group, and a Carbon-Carbon Double Bond Disposed Between the Electron Withdrawing Group and the Leaving Group In certain embodiments, the (ii) unsaturated fatty acid having an electron withdrawing group, a leaving group, and a carbon-carbon double bond disposed between the electron withdrawing group and the leaving group is described, for example, in US 2018/0282528, which is incorporated herein by reference in its entirety. In some embodiments, the unsaturated fatty acids may be nitrogen oxides of activated fatty acids in which the electron withdrawing group is nitro (—$NO_2$), and in particular embodiments, the unsaturated fatty acids may be nitrogen oxides of nitroalkenes in which the electron withdrawing group is a nitro group (—$NO_2$) and the leaving group may be a nitrogen oxide, such as nitrate (—$ONO_2$) or nitrite (—ONO). In certain embodiments, the compound (a)(ii) is a prodrug wherein the nitrite or nitrate substituent is cleaved, and the olefin shifts to yield an activated nitroalkene product. As used herein an "activated fatty acid" refers to a fatty acid having at least one electron withdrawing group covalently bound to a saturated or unsaturated aliphatic chain of a fatty acid. Such activated fatty acids may include an aliphatic chain substituted by any number of electron withdrawing groups at any number of positions and such electron withdrawing groups may or may not be associated with a carbon-carbon double bond. Similarly, the nitrogen oxide derivatives of nitroalkenes may include an aliphatic chain having any number of double bonds, which may or may not be associated with an electron withdrawing group. In certain embodiments, leaving group may be positioned at the beta (β) carbon, gamma (γ) carbon, or delta (δ) carbon of the unsaturated aliphatic chain, where the electron withdrawing group is attached to the alpha (α) carbon.

For example, the compounds of some embodiments may be of the general Formula IV:

(IV)

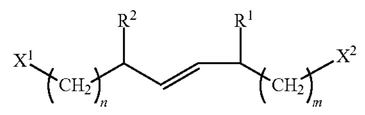

wherein $R^1$ is any electron withdrawing groups including, but not limited to —COH, —COR, —COOH, —COOR, —Cl, —F, —Br, —I, —$CF_3$, —CN, —$SO_3$, —$SO_2R$, —$SO_3H$, —$NH_3^+$, —$NH_2R^+$, —$NHR_2^+$, —$NR_3^+$ and —$NO_2$; $R^2$ is a leaving group including, but not limited to, —$OC(O)(C_{1-4})$, —$ONO_2$, —$OPO(OH)_2$, —$OSO_3$, and other inorganic esters; $X^1$ and $X^2$ are —H —COH, —COR, —COOH, —COOR, —$COCF_3$, and —$CF_2R$; and m and n are, independently, an integer from 1 to 10, and compositions containing the same.

Compounds in still other embodiments, may be of general Formula V:

(V)

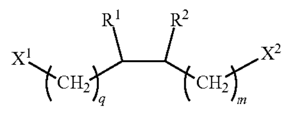

wherein $R^1$ is —H or any electron withdrawing groups including, but not limited to —COH, —COR, —COOH, —COOR, —Cl, —F, —Br, —I, —$CF_3$, —CN, —$SO_3$—, —$SO_2R$, —$SO_3H$, —$NH_3^+$, —$NH_2R^+$, —$NHR_2^+$, —$NR_3^+$ and —$NO_2$; $R^2$ is a leaving group including, but not limited to, —$OC(O)(C_{1-4})$, —$ONO_2$, —$OPO(OH)_2$, —$OSO_3$, and other inorganic esters; $X^1$ and $X^2$ are —H —COH, —COR, —COOH, —COOR, —$COCF_3$, and —$CF_2R$; and m and n are, independently, an integer from 1 to 10, and compositions containing the same.

In certain embodiments, the nitrogen oxides of nitroalkenes may be of the general Formula VI:

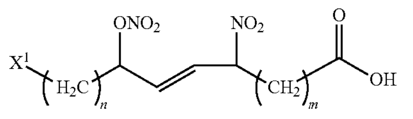

wherein $X^1$ is H, n is from 1 to 10 and m is from 1 to 10.

In some embodiments, the nitrogen oxides of nitroalkene may be of Formula VII:

(VII)

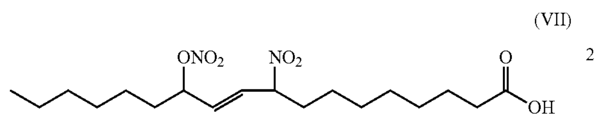

In certain embodiments, the nitrogen oxide of nitroalkene of Formula VI is (E)-9-nitro-12-(nitrooxy)octadec-10-enoic acid, nitrogen oxides of conjugated linoleic acid, or $NO_2$—$NO_3$—CLA.

In such embodiments, the electron withdrawing group may be positioned in either E or Z configuration in the original double bond or in either R or S absolute stereochemistry at an $sp^3$ chiral/stereogenic center. For example, in one embodiment, a nitroxide derivative of nitroalkenes may have one electron withdrawing group, and in another, a nitroxide derivative of nitroalkenes may be substituted with multiple electron withdrawing groups at multiple positions along the hydrocarbon chain. While the reversible nitroxide derivatives of nitroalkenes may have an electron withdrawing group positioned at any carbon along the aliphatic hydrocarbon chain between the carboxy terminal carbon to the terminal methyl (ω-position), in some embodiments, the electron withdrawing group may be positioned within about 3 carbons of either the carboxy terminal carbon and/or the methyl terminal carbon, and in other embodiments, the electron withdrawing group may be positioned within 5 carbons of either of the carboxy terminal carbon and/or the methyl terminal carbon. In still other embodiments, the electron withdrawing group may be positioned within 7 carbons of either of the carboxy terminal carbon and/or the methyl terminal carbon, and in further embodiments, the electron withdrawing group may be positioned within 9 carbons of either of the carboxy terminal carbon and/or the methyl terminal carbon.

In certain embodiments, the electron withdrawing group may be positioned on a carbon originating from a double bond of the activated fatty acid forming an "electron withdrawing vinyl" group. The electron withdrawing group of such vinyl groups may be on either side of the double bond. Fatty acids may have one or more than one electron withdrawing vinyl groups at any carbon on the aliphatic hydrocarbon chain, and there are several ways that an unsaturated fatty acid can have one electron-withdrawing group. In one embodiment, a reversible nitrogen oxides of oleic acid (octadec-9-enoic acid, OA) which originates from an 18 carbon, ω-9 fatty acid with one double bond (denoted "18:1") between the 9 h (C-9) and 10th (C-10) carbons, may have an electron withdrawing group at either C-9 or C-10, and a leaving group at the alternate position. In another exemplary embodiment, nitrogen oxides of linoleic acid (octadeca-9,12,-dienoic acid), which originated from an 18 carbon, ω-6 fatty acid with two double bonds (denoted "18:2") between the ω-6 (C-13) and -7 (C-12) carbons and the ω-9 (C-10) and 10 (C-9) carbons, may have an electron withdrawing group at C-9 or C-10, or C-12 or C-13, a leaving group at the corresponding alternate neighboring position, and at least one carbon-carbon double bond positioned between the electron withdrawing group and the leaving group. In another embodiment, a reversible nitrogen oxide of linoleic acid may have an electron withdrawing group at C-9 or C-10, or C-12 or C-13, a leaving group at the corresponding alternate neighboring position, and at least one carbon-carbon double bond adjacent to the leaving group. Similarly, other polyunsaturated fatty acids, originally having 3, 4, 5, 6 or more double bonds, can have one electron withdrawing at either position on any of the original double bond carbons, and a leaving group at the corresponding alternate position, with a carbon-carbon single bond between the electron withdrawing group and the leaving group including all possible permutations of positions and electron withdrawing groups.

The term "electron-withdrawing group" is recognized in the art and denotes the tendency of a substituent to attract valence electrons from neighboring atoms, i.e., the substituent is electronegative with respect to neighboring atoms. The term "nucleophile" or "electron-donating group" is recognized in the art and denotes the tendency of a substituent to donate excess valence electrons from neighboring atoms, i.e., the substituent is electropositive with respect to neighboring atoms. A quantification of the level of electron withdrawing capability is given by the Hammett sigma (a) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example, the Hammet constant for para substituted $NH_2$ (σ [P]) is about −0.7 and the σ [P] for a nitro group is about +0.8.

Embodiments encompass any known electron withdrawing group. For example, electron-withdrawing groups may include, but are not limited to, aldehyde (—COH), acyl (—COR), carboxylic acid (—COOH), ester (—COOR), halides (—Cl, F, —Br, etc.), fluoromethyl (—$CF_3$), fluoroalkyl (—$CF_nH_{2-n}R$), cyano (—CN), sulfoxide (—SOR), sulfonyl (—$SO_2R$), sulfonate ($SO_3R$), 1°, 2° and 3° ammonium (—$NR_3^+$), and nitro (—$NO_2$) where each R may, independently, be hydrogen, methyl, or $C_2$ to $C_6$ alkyl, alkenyl, or alkynyl. In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium or sulfonyl.

The term "leaving group" is recognized in the art and denotes the tendency of a substituent to leave a parent molecule with a pair of electrons during heterolytic bond cleavage. Leaving groups encompassed include, for example, —$OC(O)(C_{1-4})$, —$ONO_2$, —$OPO(OH)_2$, —$OSO_3$, other inorganic esters, and the like.

The fatty acids of embodiments may be any unsaturated and polyunsaturated fatty acid known in the art. The term "fatty acid" describes aliphatic monocarboxylic acids. Various embodiments include activated fatty acids having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons, and others include fatty acids having from 12 to 18 carbons in the aliphatic hydrocarbon chain. In still other embodiments, fatty acids may have greater than 24 carbons in the aliphatic hydrocarbon chain. Embodiments encompass such naturally occurring fatty acids as well as non-naturally occurring fatty acids, which may contain an odd number of carbons and/or a non-naturally occurring linker including heteroatoms. Thus, some embodiments include fatty acids having an odd number of carbons of, for example, from 5 to 23 carbons, and in other embodiments, from 11 to 17 carbons. In yet other embodiments, the fatty acids of embodiments may have greater than 23 carbons. The naturally and non-naturally occurring fatty acids may also be branched at one or more location along the hydrocarbon chain, and in various embodiments, each branch may include an aliphatic hydrocarbon chain of from 1 to 24 carbons, 2 to 20 carbons or 4 to 18 carbons wherein each branch may have an even or odd number of carbons.

The aliphatic hydrocarbon chain of fatty acids of various embodiments may be unsaturated or polyunsaturated. The term “unsaturated” refers to a fatty acid having a aliphatic hydrocarbon chain that includes at least one double bond and/or substituent. In contrast, a “saturated” hydrocarbon chain does not include any double bonds or substituents. Thus, each carbon of the hydrocarbon chain is ‘saturated’ and has the maximum number of hydrogens. “Polyunsaturated,” generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term “cis,” refers to a double bond in which carbons adjacent to the double bond are on the same side and the term “trans” refers to a double bond in which carbons adjacent to the double bond are on opposite sides. Typically, “cis” is the same as Z, and “trans” is the same as E but sometimes the IUPAC rules for naming compounds will give the opposite of this for non-carbon substituents, which is the typical case in nitroalkenes. For example, a nitroalkene can have the two carbon groups “cis” but the two groups that take priority for the naming of compounds (a nitro group on one carbon of the alkene and a carbon group on the other carbon of the alkene) are on opposite sides and thus are E. Therefore, the nitroalkene analog of a “cis” double bond is termed an E nitroalkene. Similarly, the nitroalkene analog of a “trans” double bond is termed a Z nitroalkene. Without wishing to be bound by theory, double bonds in cis configuration along the carbon chain (cis carbon chain but E nitroalkene) may induce a bend in the hydrocarbon chain. Double bonds in “trans,” configuration along the carbon chain (trans carbon chain but Z nitroalkene) may not cause the hydrocarbon chain to bend. Embodiments may include reversible nitroxide derivatives of nitroalkenes having double bonds in either E or Z configuration, and encompass compositions that may include combinations of cis and trans containing nitroxide derivatives of nitroalkenes and regioisomers of the nitroxide derivatives of nitroalkenes.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega (ω)-3, ω-5, ω-6, ω-7, ω-9 carbon-carbon double bonds. Any such fatty acid may be useful in the compounds. The symbol ‘ω’ is used to refer to the terminal methyl carbon of the aliphatic hydrocarbon chain. The placement of the double bond of the ω-X fatty acid is the carbon-carbon bond X number of carbons from the ω carbon. For example, an ω-6 fatty acid has a double bond between the $6^{th}$ and 7th carbons counting backward from the ω-carbon and an ω-3 fatty acid has a double bond between the 3rd and 4th carbons counting backward from the ω-carbon. Various embodiments include nitrated ω-3 fatty acids, including, but not limited to, linolenic acid, alphalinolenic acid, eicosapentanoic acid, docosapentaenoic acid, docosahexanoic acid and stearidonic acid; nitrated ω-5 fatty acids including, but not limited to, myristoleic acid; nitrated ω-6 fatty acids including, but not limited to, linoleic acid, gamma-linoleic acid, dihomo-gamma-linoleic acid and arachidonic acid; nitrated ω-7 fatty acids including, but not limited to, conjugated linoleic and palmitoleic acid; and nitrated ω-9 fatty acids including, but not limited to, oleic acid and erucic acid. Of course, the fatty acids may also be referred to using IUPAC nomenclature in which the placement of the double bond is determined by counting from the carbon of the carboxylic acid, and ‘C-X’ denotes the carbon in aliphatic hydrocarbons using IUPAC nomenclature wherein X is the number of the carbon counting from the carboxylic acid (including the carbonyl carbon itself). Embodiments also include synthetic equivalents to naturally occurring fatty acids and derivatives thereof.

Other embodiments include unsaturated or polyunsaturated non-naturally occurring fatty acids which may have an odd number of carbons such as, for example, 5, 7, 9, 11, 13, 15, 17, 19, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring fatty acids may include one or more linker groups, which interrupt the aliphatic hydrocarbon chain. For example, in some embodiments, activated fatty acids may have one or more non-carbon-carbon linkage such as, for example, ester, ether, vinyl ether, thioether, amino, imine and the like at any position within the aliphatic hydrocarbon chain.

In still other embodiments, the carboxy-terminal end of the nitrogen oxides of activated fatty acid may be modified. For example, in some embodiments, the nitrogen oxides of activated fatty acid may include a glycerol associated with the carboxy-terminal end of the fatty acid to create a glycerolipid, and such glycerolipids may be mono-, di-, or tri-glycerides wherein at least one of the fatty acids of a di or tri-glyceride may be an activated-nitrate fatty acid and any remaining fatty acids may be a saturated or unsaturated fatty acid. Similarly, in other embodiments, a carbohydrate may be associated with the carboxy-terminal end of an nitrogen oxides activated fatty acid to form a glycolipid. In such embodiments, any carbohydrate known in the art may be a carbohydrate moiety of a glycolipid including, but not limited to, galactose and glucose. In yet other embodiments, a carbohydrate may be associated with a glyceride which is associated with the carboxy-terminal end of an activated-nitrate fatty acid to form a glycero-glycolipid, which may have one or two activated fatty acids associated with the glycero-portion of the glycero-glycolipid and, in embodiments in which only one activated fatty acid is associated with the glycero-glycolipid, the remaining position on the glycerol may include a saturated or unsaturated fatty acid or hydrogen, alkyl, or a functional group such as, for example, alcohol, amine, phosphate, phosphonic acid, thiol, sulfonic acid and the like. In certain embodiments, the carboxy-terminal end of the activated fatty acids may be associated with a phosphate to form a phospholipid. In such embodiments, the phosphate may be directly associated with the fatty acid through the carboxy-terminus, or the phosphate may be associated with a di-glyceride wherein one or two activated fatty acids are attached glycerol moiety and, in embodiments where only one activated-nitrate the fatty acid is attached to the glycerol, remaining position on the glycerol may include a saturated or unsaturated fatty acid or hydrogen, alkyl, or a functional group such as, for example, alcohol, amine, phosphate, phosphonic acid, thiol, sulfonic acid and the like. In further embodiments, the carboxy-terminus of the activated fatty acid may be associated with a cholesterol or other sterol moiety. In yet other embodiments, the carboxy-terminal end may be modified by the covalent attachment of a secondary active agent. In particular embodiments, carboxy-terminal modifications including a glycerol may not include a nitro group. Without wishing to be bound by theory, modification of the carboxy-terminal end of activated-nitrate fatty acids may enhance partitioning of the activated fatty acid after administration and may also improve resilience of the activated fatty acid by inhibiting beta-oxidation in mitochondria following administration.

Compound (iii)—Thiol-Adducted Nitro Fatty Acid ("Thiolated Fatty Acid")

A potential barrier to the use of nitro-oleic acid as a drug candidate is its rapid metabolism as a result of beta-oxidation reactions and reduction of the nitroalkene by Prostaglandin Reductase 1, in the liver first pass and reversible adduction with glutathione and excretion. To increase efficacy, the drug must withstand the first pass metabolism. An active drug would be metabolized within the gut microbiome and liver, and thus must be protected in order to appropriately deliver an effective amount of the active drug into circulation.

The modification of nitroalkene fatty acids by reversible thiolation of the nitroalkene prevents its metabolic inactivation, thus preserving the potential electrophilic character of the nitroalkene fatty acid. Upon dissociation of the thiol or poly thiol substituent, the "activated" nitroalkene product become competent to target functionally significant nucleophilic residues in RAD51 or other DNA repair proteins.

Examples of thiolated fatty acids are described, for example, in US 2019/0282527, which is incorporated herein by reference in its entirety.

Embodiments are generally directed to thiolated electrophilic unsaturated activated fatty acids and, in particular, thiolated unsaturated nitrated fatty acids. As used herein an "activated fatty acid" refers to a fatty acid having at least one electron withdrawing group covalently bound to an unsaturated carbon of the saturated or unsaturated aliphatic chain of a fatty acid. Such activated fatty acids may include an aliphatic chain substituted by any number of electron withdrawing groups at any number of positions on the hydrocarbon chain and such electron withdrawing groups may or may not be associated with a carbon-carbon double bond. Similarly, the thiolated activated fatty acids described herein may include an aliphatic chain having any number of double bonds, which may or may not be associated with an electron withdrawing group, and a sulfur containing group, i.e. a thiol group. In certain embodiments, the sulfur containing group may be positioned at the beta (□) carbon, gamma (□) carbon, or delta (□) carbon of the unsaturated aliphatic chain, where the electron withdrawing group is attached to the alpha (□) carbon.

The electrophilic double bond of the nitroalkene is reversibly protected by $H(S)_xR$ forming the thiolated-activated fatty acid. This thiolated-activated fatty acid is now a prodrug and avoids metabolic processes during first pass. The electrophilic double bond is regenerated following the loss of the protective group, as depicted below:

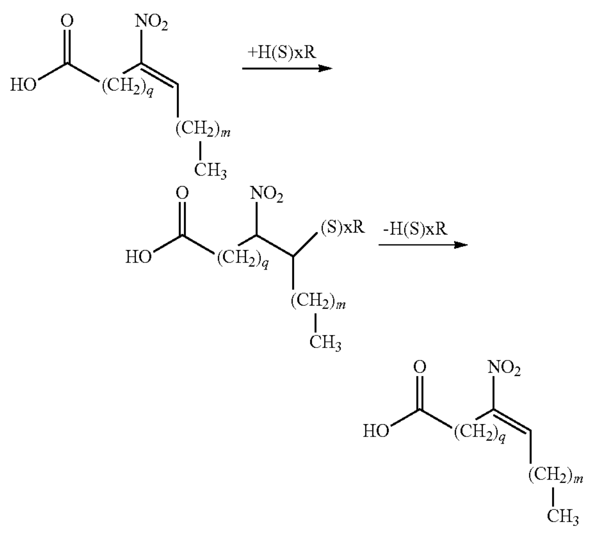

For example, thiolated activated fatty acids of some embodiments may be of general Formula VIII:

(VIII)

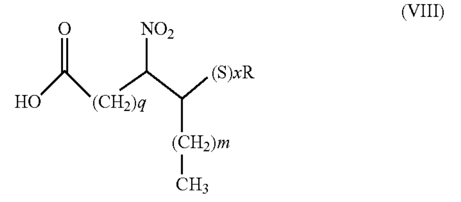

wherein R is hydrogen (—H), methyl, or $C_2$ to $C_6$ alkyl, alkenyl, or alkynyl, or (S)xR may be a sulfur containing functional group such as, sulfino (—SOOH), sulfo (—SOOOH), or thiocyanate (—SCN), x is an integer from 1 to 5, and q and m are each, independently, an integer from 1 to 10. Compounds of Formula VIII include a sulfur containing group at the □ carbon.

Other thiolated activated fatty acids include compounds of the general Formula IX:

(IX)

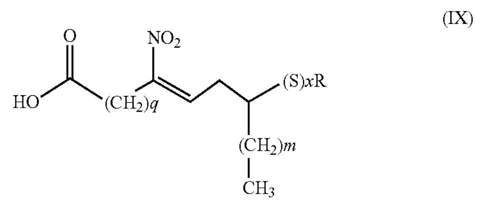

wherein R is hydrogen (—H), methyl, or $C_2$ to $C_6$ alkyl, alkenyl, or alkynyl, or (S)xR may be a sulfur containing functional group such as, sulfino (—SOOH), sulfo (—SOOOH), or thiocyanate (—SCN), x is an integer from 1 to 5, and q and m are each, independently, an integer from 1 to 10. Compounds of Formula IX include a sulfur containing group at the □ carbon.

In some embodiments, R for Formulae VIII or IX may be a bifunctional alkyl, alkenyl, or alkynyl, that is attached to the carboxyl of the activated fatty acid forming bridged or cyclic structures. In such embodiments, the sulfur containing moiety may be positioned at either □, □, or □ carbon. For example, the compounds of the general Formulae Xa and Xb, which include cyclized bifunctional sulfur containing moieties at the □ carbon:

(Xa)

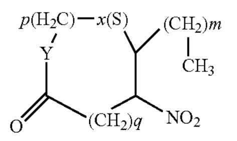

(Xb)

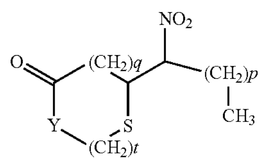

wherein each Y is, independently, oxygen (O) or nitrogen (N), each x is, independently, an integer from 1 to 5, and q, m, p, and t are each, independently, an integer from 1 to 10. In some embodiments, the sulfur containing group may join two activated fatty acids. For example, various embodiments of the invention are directed to compounds of the general Formula XI:

(XI)

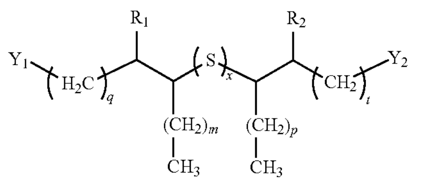

wherein $R_1$ and $R_2$ are independently selected from —H and any electron withdrawing groups including, but not limited to —COH, —COR, —COOH, —COOR, —Cl, —F, —Br, —I, —$CF_3$, —CN, —$SO_3$—, —$SO_2R$, —$SO_3H$, —$NH_3^+$, —$NH_2R^+$, —$NHR_2^+$, —$NR_3^+$ and —$NO_2$; wherein at least one of $R_1$ and $R_2$ is an electron withdrawing group; wherein $Y_1$ and $Y_2$ are independently selected from —H, —COH, —COR, —COOH, and —COOR; wherein at least one of $R_1$ and $R_2$ is an electron withdrawing group; and wherein x is an integer from 1 to 5, and q, m, p, and t are, independently, an integer from 1 to 10, and compositions containing the same.

Various embodiments of the invention are directed to compounds of the general Formulas XIIa, XIIb, and XIIc:

(XIIa)

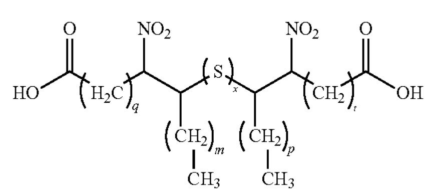

(XIIb)

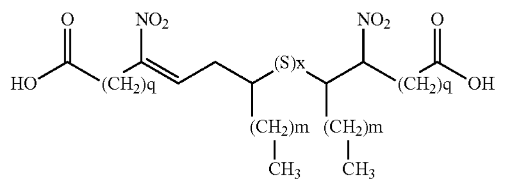

(XIIc)

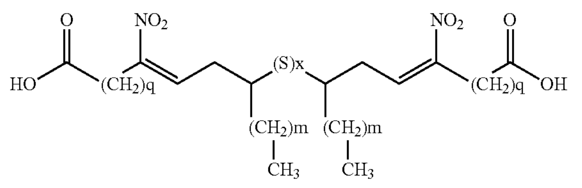

wherein x is an integer from 1 to 5, and q, m, p, and t are, independently, an integer from 1 to 10, and compositions containing the same.

Other embodiments, include compounds of Formula XIII:

(XIII)

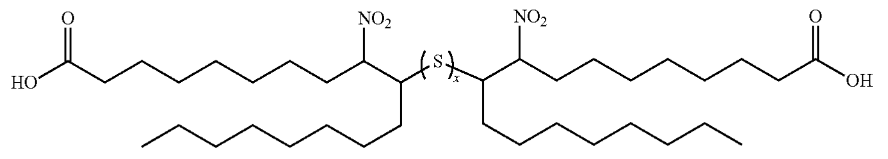

wherein x is an integer from 1 to 5, and compositions containing the same.

In some embodiments, the compound is a thiolated nitro-oleic acid ($NO_2$—OA-$S_x$) species depicted as Formula XIV:

(XIV)

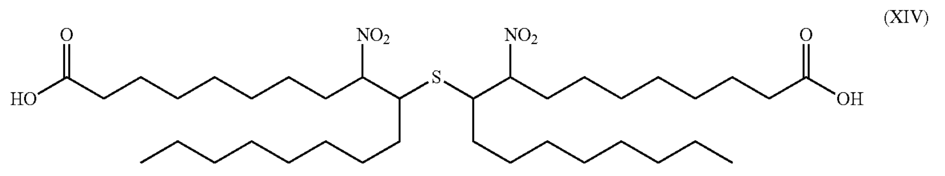 [SMILES: CCCCCCCCC(SC(CCCCCCCC)C(CCCCCCCC(=O)O)[N+](=O)[O-])C(CCCCCCCC(=O)O)[N+](=O)[O-]]

The electron withdrawing group may be positioned in either cis or trans configuration in the original double bond or in either R or S absolute stereochemistry at an $sp^3$ chiral/stereogenic center. For example, in one embodiment, a thiolated activated fatty acid may have one electron withdrawing group, and in another, a thiolated activated fatty acid may be substituted with multiple electron withdrawing groups at multiple positions along the hydrocarbon chain. While the thiolated activated fatty acids may have an electron withdrawing group positioned at any carbon along the aliphatic hydrocarbon chain between the carboxy terminal carbon to the terminal methyl (ω-position), in some embodiments, the electron withdrawing group may be positioned within about 3 carbons of either the carboxy terminal carbon and/or the methyl terminal carbon, and in other embodiments, the electron withdrawing group may be positioned within 5 carbons of either of the carboxy terminal carbon and/or the methyl terminal carbon. In still other embodiments, the electron withdrawing group may be positioned within 7 carbons of either of the carboxy terminal carbon and/or the methyl terminal carbon, and in further embodiments, the electron withdrawing group may be positioned within 9 carbons of either of the carboxy terminal carbon and/or the methyl terminal carbon.

In certain embodiments, the electron withdrawing group may be positioned on a carbon originating from a double bond of the activated fatty acid forming an "electron withdrawing vinyl" group. The electron withdrawing group of such vinyl groups may be on either side of the double bond. Fatty acids may have one or more than one electron withdrawing vinyl groups at any carbon on the aliphatic hydrocarbon chain, and there are several ways that an unsaturated fatty acid can have one electron-withdrawing group. In one embodiment, a thiolated activated oleic acid (octadec-9-enoic acid) which originates from an 18 carbon, ω-9 fatty acid with one double bond (denoted "18:1") between the 9 h (C-9) and 10th (C-10) carbons, may have an electron withdrawing group at either C-9 or C-10, and a thiol (—SR) at the alternate position. In another exemplary embodiment, a thiolated activated linoleic acid (octadeca-9,12,-dienoic acid), which originated from an 18 carbon, ω-6 fatty acid with two double bonds (denoted "18:2") between the ω-6 (C-13) and -7 (C-12) carbons and the ω-9 (C-10) and 10 (C-9) carbons, may have an electron withdrawing group at C-9 or C-10, or C-12 or C-13, and a thiol (—SR) at the corresponding alternate neighboring position. Similarly, other polyunsaturated fatty acids, originally having 3, 4, 5, 6 or more double bonds, can have one electron withdrawing at either position on any of the original double bond carbons, and a thiol (—SR) at the corresponding alternate neighboring position, including all possible permutations of positions and electron withdrawing groups.

In other embodiments, a mono or polyunsaturated fatty acid may have two electron-withdrawing groups, and there are several ways that an unsaturated fatty acid can have two electron-withdrawing groups. For example, in one embodiment, a thiolated activated linoleic acid (octadeca-9,12,-dienoic acid), which originates from an 18 carbon, ω-6 fatty acid with two double bonds (denoted "18:2") between the ω-6 (C-13) and -7 (C-12) carbons and the ω-9 (C-10) and 10 (C-9) carbons, may have an electron withdrawing group at any two of the positions C-9, C-10, C-12 or C-13, with the following possible permutations: C-9 and C-12, C-9 and C-13, C-10 and C-12, or C-10 and C-13, and one or more thiols (—SR) at the corresponding alternate neighboring positions.

In analogy to the preceding descriptions of compounds with one electron withdrawing group or two electron-withdrawing groups, it is also possible to have three, four, five or more electron withdrawing groups. Following the same logic above, in the preceding descriptions of compounds with one electron-withdrawing group or two electron-withdrawing groups, polyunsaturated fatty acids, with 3, 4, 5, 6 or more double bonds, conjugated or non-conjugated, can have multiple electron withdrawing (three, four, five or more, as available positions for substitution permit) at any of the positions on any of the double bond carbons, including all possible permutations of positions, nucleophilic substituents, and electron-withdrawing groups. Additionally, in any embodiments such as those described above, any number of non-electron-withdrawing groups may be covalently bound to carbons of the aliphatic chain of the activated fatty acid. For example, in some embodiments, the thiolated activated fatty acids may include one or more methyl, $C_2$-$C_6$ alkyl, alkenyl, or alkynyl or amino covalently attached to one or more carbons of the aliphatic chain of a thiolated activated fatty acid.

The term "electron-withdrawing group" is recognized in the art and denotes the tendency of a substituent to attract valence electrons from neighboring atoms, i.e., the substituent is electronegative with respect to neighboring atoms. The term "nucleophile" or "electron-donating group" is recognized in the art and denotes the tendency of a substituent to donate excess valence electrons from neighboring atoms, i.e., the substituent is electropositive with respect to neighboring atoms. A quantification of the level of electron withdrawing capability is given by the Hammett sigma (a) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example, the Hammet constant for para substituted $NH_2$ (σ [P]) is about −0.7 and the σ [P] for a nitro group is about +0.8.

Embodiments encompass any known electron withdrawing group. For example, electron-withdrawing groups may include, but are not limited to, aldehyde (—COH), acyl (—COR), carboxylic acid (—COOH), ester (—COOR), halides (—Cl, F, —Br, etc.), fluoromethyl (—$CF_3$), fluoroalkyl ($—CF_nH_{2-n}R$), cyano (—CN), sulfoxide (—SOR), sulfonyl ($—SO_2R$), sulfonate ($SO_3R$), 1°, 2° and 3° ammonium ($—NR_3^+$), and nitro ($—NO_2$) where each R may, independently, be hydrogen, methyl, or $C_2$ to $C_6$ alkyl, alkenyl, or alkynyl. In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium or sulfonyl. In other embodiments, the thiolated activated fatty acids may be additionally substituted by non-electron withdrawing groups or electron donating groups including, for example, thiol (—SR), alcohol (—OH), reverse ester (—OOCR), alkyl, alkenyl, alkynyl, 1° and 2° amines ($—NR_2$), N-containing heterocycle (—N═, —NR—), nitrate ($—ONO_2$), nitrito (—ONO) and the like.

The fatty acids of embodiments may be any unsaturated and polyunsaturated fatty acid known in the art. The term "fatty acid" describes aliphatic monocarboxylic acids. Various embodiments include activated fatty acids having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons, and others include fatty acids having from 12 to 18 carbons in the aliphatic hydrocarbon chain. In still other embodiments, fatty acids may have greater than 24 carbons in the aliphatic hydrocarbon chain. Embodiments encompass such naturally occurring fatty acids as well as non-naturally occurring fatty acids, which may contain an odd number of carbons and/or a non-naturally occurring linker including heteroatoms. Thus, some embodiments include fatty acids having an odd number of carbons of, for example, from 5 to 23 carbons, and in other embodiments, from 11 to 17 carbons. In yet other embodiments, the fatty acids of embodiments may have greater than 23 carbons. The naturally and non-naturally occurring fatty acids may also be branched at one or more location along the hydrocarbon chain, and in various embodiments, each branch may include an aliphatic hydrocarbon chain of from 1 to 24 carbons, 2 to 20 carbons or 4 to 18 carbons wherein each branch may have an even or odd number of carbons.

The aliphatic hydrocarbon chain of fatty acids of various embodiments may be unsaturated or polyunsaturated. The term "unsaturated" refers to a fatty acid having a aliphatic hydrocarbon chain that includes at least one double bond and/or substituent. In contrast, a "saturated" hydrocarbon chain does not include any double bonds or substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically, "cis" is the same as Z, and "trans" is the same as E but sometimes the IUPAC rules for naming compounds will give the opposite of this for non-carbon substituents, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore the nitroalkene analog of a "cis" double bond is termed an E nitroalkene. Similarly, the nitroalkene analog of a "trans" double bond is termed a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend. Embodiments may include thiolate activated fatty acids having double bonds in either cis or trans configuration, and encompass compositions that may include combinations of cis and trans containing thiolated activated fatty acids and regioisomers of the thiolated activated fatty acids.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega (ω)-3, ω-5, ω-6, ω-7, ω-9 carbon-carbon double bonds. Any such fatty acid may be useful. The symbol 'ω' is used to refer to the terminal methyl carbon of the aliphatic hydrocarbon chain. The placement of the double bond of the ω-X fatty acid is the carbon-carbon bond X number of carbons from the ω carbon. For example, an ω-6 fatty acid has a double bond between the $6^{th}$ and 7th carbons counting backward from the ω-carbon and an ω-3 fatty acid has a double bond between the 3rd and 4th carbons counting backward from the ω-carbon. Various embodiments include nitrated ω-3 fatty acids, including, but not limited to, linolenic acid, alphalinolenic acid, eicosapentanoic acid, docosapentaenoic acid, docosahexaenoic acid and stearidonic acid; nitrated ω-5 fatty acids including, but not limited to, myristoleic acid; nitrated ω-6 fatty acids including, but not limited to, linoleic acid, gamma-linoleic acid, dihomo-gamma-linoleic acid and arachidonic acid; nitrated ω-7 fatty acids including, but not limited to, conjugated linoleic and palmitoleic acid; and nitrated ω-9 fatty acids including, but not limited to, oleic acid and erucic acid. Of course, the fatty acids may also be referred to using IUPAC nomenclature in which the placement of the double bond is determined by counting from the carbon of the carboxylic acid, and 'C-X' denotes the carbon in aliphatic hydrocarbons using IUPAC nomenclature wherein X is the number of the carbon counting from the carboxylic acid (including the carbonyl carbon itself). Embodiments also include synthetic equivalents to naturally occurring fatty acids and derivatives thereof.

Other embodiments include unsaturated or polyunsaturated non-naturally occurring fatty acids which may have an odd number of carbons such as, for example, 5, 7, 9, 11, 13, 15, 17, 19, 20, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring fatty acids may include one or more linker groups, which interrupt the aliphatic hydrocarbon chain. For example, in some embodiments, activated fatty acids may have one or more non-carbon-carbon linkage such as, for example, ester, ether, vinyl ether, thioether, amino, imine and the like at any position within the aliphatic hydrocarbon chain.

Various embodiments include unsaturated or polyunsaturated fatty acids that may have a carbon-carbon double bond between any two carbons of the aliphatic chain of the fatty acid, and any number of carbon-carbon double bonds may be present in such polyunsaturated fatty acids. For example, in some embodiments, polyunsaturated fatty acids may have 2, 3, 4, 5, 6 or more carbon-carbon double bonds. In such embodiments, each of the more than one carbon-carbon double bond may individually be in either cis or trans configuration. In some embodiments, thiolated activated fatty acids are derived from reaction with at least one of the carbon-carbon double bonds of a polyunsaturated fatty acid which has an associated electron withdrawing group, and in other embodiments, more than one of the carbon-carbon double bonds of such polyunsaturated fatty acids may have an associated electron withdrawing group. Additionally, in such embodiments, the electron withdrawing group may be associated with either carbon of the original carbon-carbon double bond or a carbon directly adjacent to either carbon of the carbon-carbon double bond, and the thiol may be associated with the other carbon of the original carbon-carbon double bond or a carbon directly adjacent to either carbon of the carbon-carbon double bond. For example, in some embodiments, an electron withdrawing group may be attached to the alpha ($\alpha$) carbon of the former carbon-carbon double bond, and in other embodiments, an electron withdrawing group may be associated with the beta ($\beta$) carbon of the former carbon-carbon double bond. In those embodiments, a thiol would be attached respectively to the beta ($\beta$) carbon of the former carbon-carbon double bond, and in other embodiments, an electron withdrawing group may be associated with the alpha ($\alpha$) carbon of the former carbon-carbon double bond.

In particular embodiments, an unsaturated fatty acid having at least one electron withdrawing group may be a conjugated fatty acid. In such embodiments, two carbon-carbon double bonds in an aliphatic chain are adjacent to one another such that there is no methylene group between them. Such conjugated compounds are commonly called 1,3-dienes, or conjugated fatty acids. Such 1,3-dienes may include one or more electron withdrawing groups at any of 6 positions, at the 1, 2, 3, and/or 4 positions of the 1,3-dienes and at the two carbons adjacent to the diene (at the 0 and 5 positions, in relation to the 1, 2, 3, 4 method of identifying carbons in a 1,3-diene). For example, one associated electron withdrawing group may be attached to any of the 6 positions identified above, that is to either the 1, 2, 3, or 4 positions on the diene or to either of the carbons adjacent to the 1,3-diene (at the 0 or 5 positions, as described above). In additional embodiments, two associated electron withdrawing groups could be attached to any two of the six possible positions, three associated electron withdrawing groups could be attached to any two of the six possible positions, four associated electron withdrawing groups could be attached to any two of the six possible positions, five associated electron withdrawing groups could be attached to any two of the six possible positions, and six associated electron withdrawing groups could be attached to any two of the six possible positions. In summary, any configuration of electron withdrawing groups attached to any of the six positions described above in a 1,3-diene are encompassed by embodiments of the compound.

In certain embodiments, the thiolated activated fatty acids may undergo an isomerization following preparation such that either the cis/trans configuration of the double bond, the location of the double bond in the carbon chain, or both, may change. For example, in some embodiments, a thiolated activated fatty acid may be prepared from a carbon-carbon double bond of having an electron withdrawing group attached to a gamma carbon of a carbon-carbon double bond. Following preparation, the carbon-carbon double bond may undergo an isomerization such that the electron withdrawing group is now conjugated with the carbon-carbon double bond after isomerization. Such isomerizations may occur spontaneously at any time following preparation, and may result in a composition which may have initially been prepared as including a single species of a thiolated activated fatty acid that subsequently includes a combination of isomers of the first-prepared activated fatty acid originally produced.

In still other embodiments, the carboxy-terminal end of the thiolated activated fatty acid may be modified. For example, in some embodiments, the thiolated activated fatty acid may include a glycerol associated with the carboxy-terminal end of the fatty acid to create a glycerolipid, and such glycerolipids may be mono-, di-, or tri-glycerides wherein at least one of the fatty acids of a di or tri-glyceride may be a thiolated activated fatty acid and any remaining fatty acids may be a saturated or unsaturated fatty acid. Similarly, in other embodiments, a carbohydrate may be associated with the carboxy-terminal end of a thiolated activated fatty acid to form a glycolipid. In such embodiments, any carbohydrate known in the art may be a carbohydrate moiety of a glycolipid including, but not limited to, galactose and glucose. In yet other embodiments, a carbohydrate may be associated with a glyceride which is associated with the carboxy-terminal end of a thiolated activated fatty acid to form a glycero-glycolipid, which may have one or two activated fatty acids associated with the glycero-portion of the glycero-glycolipid and, in embodiments in which only one activated fatty acid is associated with the glycero-glycolipid, the remaining position on the glycerol may include a saturated or unsaturated fatty acid or hydrogen, alkyl, or a functional group such as, for example, alcohol, amine, phosphate, phosphonic acid, thiol, sulfonic acid and the like. In certain embodiments, the carboxy-terminal end of the activated fatty acids may be associated with a phosphate to form a phospholipid. In such embodiments, the phosphate may be directly associated with the fatty acid through the carboxy-terminus, or the phosphate may be associated with a di-glyceride wherein one or two activated fatty acids are attached glycerol moiety and, in embodiments where only one thiolated activated the fatty acid is attached to the glycerol, remaining position on the glycerol may include a saturated or unsaturated fatty acid or hydrogen, alkyl, or a functional group such as, for example, alcohol, amine, phosphate, phosphonic acid, thiol, sulfonic acid and the like. In further embodiments, the carboxy-terminus of the activated fatty acid may be associated with a cholesterol or other sterol moiety. In yet other embodiments, the carboxy-terminal end may be modified by the covalent attachment of a secondary active agent. In particular embodiments, carboxy-terminal modifications including a glycerol may not include a nitro group. Without wishing to be bound by theory, modification of the carboxy-terminal end of thiolated activated fatty acids may enhance partitioning of the activated fatty acid after administration and may also improve resilience of the activated fatty acid by inhibiting beta-oxidation in mitochondria following administration.

The compounds increase the bioavailability of the activated fatty acid present as a dimer within the thiolated molecule. Thiolation of the electrophilic alkene protects the molecule through the first pass metabolism of the intestinal tract and liver. This protection occurs by preventing reduction of the alkene by Prostaglandin Reductase 1 and by delaying the adduction with glutathione. Further, the longer polysulfide chain the greater the stability of the molecule, providing for an extended release of the activated fatty acid in circulation. When the thioloated nitro fatty acid releases the nitro fatty acid and a hydrogen sulfide, an additional protective measure is provided.

Compound (iv)—Dicarboxylic acid compound containing an electron withdrawing group Compounds (iv) are dicarboxylic acid compounds containing electron withdrawing groups, and in some embodiments such compounds may further contain alkenes associated with the electron withdrawing groups. Various embodiments are directed to alkyl esters of dicarboxylic acid compounds containing electron withdrawing groups, and in some embodiments such compounds may further contain alkenes associated with the electron withdrawing groups. Various embodiments of the invention are directed to compounds of Formulae XV to XXIV. Such compounds are described, for example, in US 2019/0091186, which is incorporated herein by reference in its entirety. These electrophilic dicarboxylates are competent to alkylate functionally significant thiols and inactivate RAD51 or other DNA repair proteins.

The compounds may be of general Formulae XV or XVI:

XV

XVI

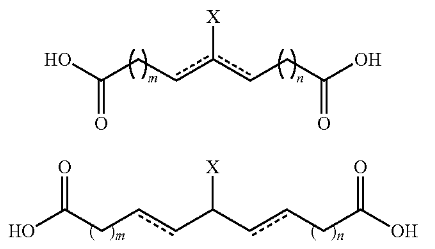

wherein X is an electron withdrawing group, each ====== can, individually, be a single or double bond, and each m and n are, independently, an integer of 1 to 10. In particular embodiments, at least one ====== depicted in Formulae XV and XVI is a double bond. In some embodiments, both ====== depicted in Formulae XV and XVI may be single bonds, and in other embodiments, both ====== depicted in Formulae XV and XVI may be double bonds. In other embodiments, the compounds may be of general Formulae XVII and XVIII:

XVII

XVIII

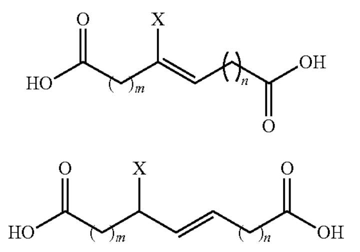

wherein X is an electron withdrawing group and each m and n are, independently, an integer of 1 to 10.

Further embodiments are directed to alkyl esters of the dicarboxylic acid compounds containing electron withdrawing groups such as, for example, compounds of general Formulae XIX and XX:

XIX

XX

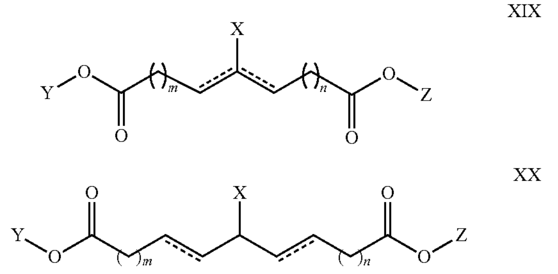

wherein X is an electron withdrawing group, each Y and Z is, individually, hydrogen or a $C_1$ to $C_{10}$ alkyl, each ====== is, individually, a single or double bond, and each m and n are, independently, absent or an integer of 1 to 10. In particular embodiments, at least one ====== depicted in Formulae XIX and XX is a double bond. In some embodiments, both ====== depicted in Formulae XIX and XX may be single bonds, and in other embodiments, both ====== depicted in Formulae XIX and XX may be double bonds. In some embodiments, the alkyl esters of dicarboxylic acid compounds containing electron withdrawing groups may be compounds of Formula XXI and XXII:

XXI

XXII

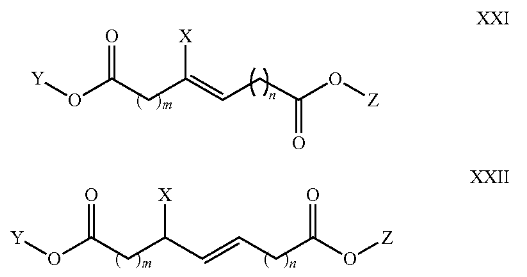

wherein X is an electron withdrawing group, each Y and Z is, individually, hydrogen or a $C_1$ to $C_{10}$ alkyl, and each m and n are, independently, an integer of 1 to 10. In certain embodiments, each Y and Z of the compounds of Formulae XIX, XX, XXI, and XXII illustrated above may be methyl ($C_1$ alkyl) or ethyl ($C_2$ alkyl).

The alkylene created by m and n in each of the compounds of Formulae XV-XXII illustrated above may include carbon-carbon double bonds in addition to the double bonds depicted in Formulae XVII, XVIII, XXI, and XXII or optionally present as indicated by ====== of Formulae XV, XVI, XIX, and XX. For Example, the compounds of some embodiments may be of Formulae XXIII and XXIV:

XXIII

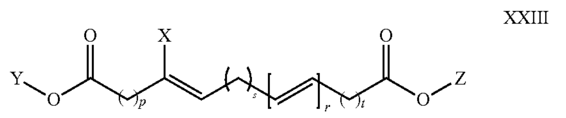

-continued

XXIV

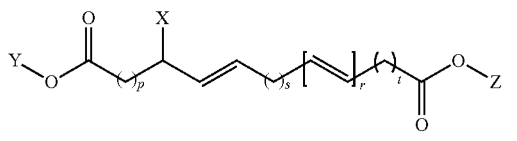

wherein X is an electron withdrawing group, each Y and Z is, individually, hydrogen or $C_1$ to $C_{10}$ alkyl, and each p and t are, independently, an integer of 1 to 10, each s is absent or an integer of 1 to 10, and each r is an integer of 1 to 5. In certain embodiments, each Y and Z of the compounds of Formulae XXIII and XXIV illustrated above may be methyl ($C_1$ alkyl) or ethyl ($C_2$ alkyl).

Additional embodiments are directed to dicarboxylic acid compounds containing electron withdrawing groups further containing at least one alkene associated with the electron withdrawing group of Formulae XV, XVII, XIX, XXI and XXIII, wherein at least one alkene associated with the electron withdrawing group has been reduced the introduction of a nucleophile "A" by means of a Michael addition reaction to yield compounds of Formulae XVA, XVIIA, XIXA, XIXB, XXIA and XXIIIA.

XVA

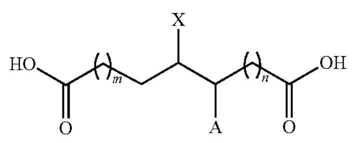

XVIIA

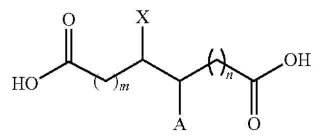

XIXA

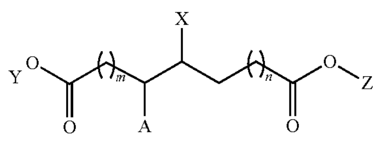

XIXB

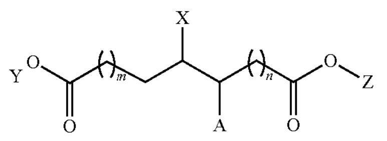

XXIA

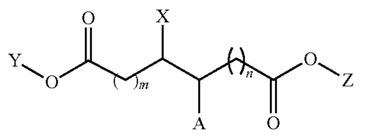

XXIIIA

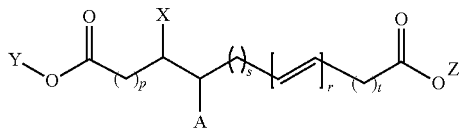

wherein X is an electron withdrawing group, A is a nucleophile, each Y and Z is, individually, hydrogen or $C_1$ to $C_{10}$ alkyl, and each m, n, p and t are, independently, an integer of 1 to 10, each s is absent or an integer of 1 to 10, and each r is an integer of 1 to 5. In certain embodiments, each Y and Z may be methyl ($C_1$ alkyl) or ethyl ($C_2$ alkyl).

It is envisioned that the compounds of Formulae XVA, XVIIA, XIXA, XIXB, XXIA and XXIIIA could be useful as either prodrugs of the compounds of Formulae XV, XVII, XIX, XXI and XXIII or as active therapeutic agents themselves. If used as prodrugs, it is envisioned that the compounds of Formulae XVA, XVIIA, XIXA, XIXB, XXIA and XXIIIA would metabolize in vivo after administration to a patient in need thereof to provide a therapeutically effective amount of the active agent according to Formulae XV, XVII, XIX, XXI and XXIII.

The term "nucleophile" is recognized in the art and denotes a chemical species that donates an electron pair to an electrophile to form a chemical bond in relation to a reaction. All molecules or ions with a free pair of electrons or at least one 7r-bond can act as electrophiles. Nucleophiles, i.e., A, may include but are not limited to, enols, hydroxide anion, alcohols, alkoxide anions, hydrogen peroxide, carboxylate anions, hydrogen sulfide, thiols, thiolate anions, anions of thiocarboxylic acids, anions of dithiocarbonates, ammonia, azide, amines and nitriles.

The term "electron-withdrawing group" is recognized in the art and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example, the Hammet constant for para substituted $NH_2$ (6[P]) is about −0.7 and the σ[P] for a nitro group is about 0.8. Electron-withdrawing groups may include, but are not limited to, aldehyde (—COH) acyl (—COR), carbonyl (—CO), carboxylic acid (—COOH), ester (—COOR), halides (—Cl, —F, —Br, etc.), fluoromethyl (—$CF_n$), cyano (—CN), sulfonyl (—$SO_n$), sulfone (—$SO_2R$), sulfonic acid (—$SO_3H$), 1°, 2°, and 3° ammonium (—$NR^{3+}$), and nitro (—$NO_2$). In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium, or sulfonyl.

In certain embodiments, the dicarboxylic acid compound has the structure:

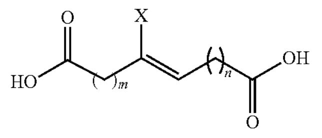

wherein m is from 1 to 10;

n is from 1 to 10;

the double bond is cis to trans; and

X is an electron withdrawing group selected from —$NO_2$, —CN, halide, $C_xF_{2x+1}$, wherein x is from 1 to 5, SOR, wherein R is H or $C_1$-$C_6$ alkyl, $SO_2R$, wherein R is H or $C_1$-$C_6$ alkyl, or $SO_3R$, wherein R is H or $C_1$-$C_6$ alkyl.

In certain embodiments, X is —$NO_2$.

In certain embodiments, the compound is an alkyl ester of a dicarboxylic acid having a structure of:

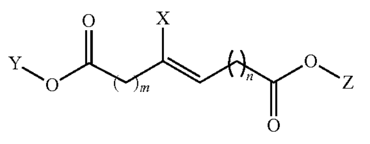

wherein m is from 1 to 10;
n is from 1 to 10;
the double bond is cis to trans;
Y and Z are each, independently a $C_1$ to $C_{10}$ alkyl, alkenyl or alkynyl;
and X is an electron withdrawing group selected from $—NO_2$, —CN, halide, $C_xF_{2x+1}$, wherein x is from 1 to 5, SOR, wherein R is H or $C_1$-$C_6$ alkyl, $SO_2R$, wherein R is H or $C_1$-$C_6$ alkyl, or $SO_3R$, wherein R is H or $C_1$-$C_6$ alkyl.
In certain embodiments, m is 2 and n is 2.
In certain embodiments, Y and Z are each, independently a $C_1$ to $C_6$ alkyl, more particularly methyl or ethyl.
In certain embodiments, X is $—NO_2$.

In certain embodiments, the compound is an alkyl ester of a dicarboxylic acid having a structure of:

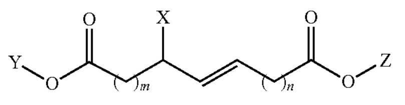

wherein m is from 1 to 10;
n is from 1 to 10;
the double bond is cis to trans;
Y and Z are each, independently a $C_1$ to $C_{10}$ alkyl, alkenyl or alkynyl;
and X is an electron withdrawing group selected from $—NO_2$, —CN, halide, $C_xF_{2x+1}$, wherein x is from 1 to 5, SOR, wherein R is H or $C_1$-$C_6$ alkyl, $SO_2R$, wherein R is H or $C_1$-$C_6$ alkyl, or $SO_3R$,
wherein R is H or $C_1$-$C_6$ alkyl.
In certain embodiments, m is 2 and n is 2.
In certain embodiments, Y and Z are each, independently a $C_1$ to $C_6$ alkyl, more particularly methyl or ethyl.
In certain embodiments, X is $—NO_2$.
In certain embodiments, the compound is:

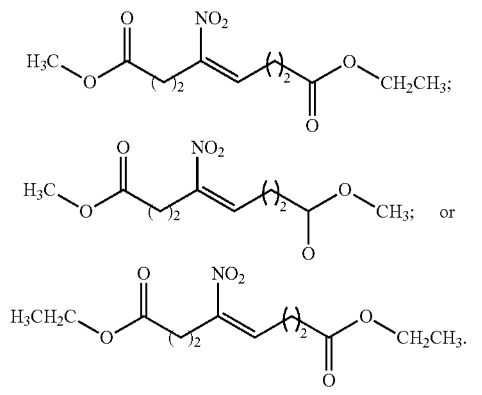

In some embodiments, the methods disclosed herein involve administering to a subject in need of treatment a pharmaceutical composition, for example a composition that includes a pharmaceutically acceptable carrier and a therapeutically effective amount of one or more of the compounds disclosed herein. The compounds may be administered orally, parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmically, or rectally. The pharmaceutical composition may be administered in dosage unit formulations containing conventional non-toxic pharmaceutically acceptable carriers, adjuvants, and/or vehicles. The compounds are preferably formulated into suitable pharmaceutical preparations such as tablets, capsules, or elixirs for oral administration or in sterile solutions, emulsions or suspensions for parenteral or topical administration or inhalation. Typically, the compounds described above are formulated into pharmaceutical compositions using techniques and procedures well known in the art.

In some embodiments, one or more of the disclosed compounds (including compounds linked to a detectable label or cargo moiety) are mixed or combined with a suitable pharmaceutically acceptable carrier to prepare a pharmaceutical composition. Pharmaceutical carriers or vehicles suitable for administration of the compounds provided herein include any such carriers known to be suitable for the particular mode of administration. *Remington: The Science and Practice of Pharmacy*, The University of the Sciences in Philadelphia, Editor, Lippincott, Williams, & Wilkins, Philadelphia, PA, $21^{st}$ Edition (2005), describes exemplary compositions and formulations suitable for pharmaceutical delivery of the compounds disclosed herein. In addition, the compounds may be formulated as the sole pharmaceutically active ingredient in the composition or may be combined with other active ingredients.

Upon mixing or addition of the compound(s) to a pharmaceutically acceptable carrier, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. Where the compounds exhibit insufficient solubility, methods for solubilizing may be used. Such methods are known and include, but are not limited to, using co-solvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions. The disclosed compounds may also be prepared with carriers that protect them against rapid elimination from the body, such as time-release formulations or coatings. Such carriers include controlled release formulations, such as, but not limited to, microencapsulated delivery systems. Formulations may also be obtained by dissolution with mid and long chain natural oils.

The disclosed compounds and/or compositions can be enclosed in multiple or single dose containers. The compounds and/or compositions can also be provided in kits, for example, including component parts that can be assembled for use. For example, one or more of the disclosed compounds may be provided in a lyophilized form and a suitable diluent may be provided as separated components for combination prior to use. In some examples, a kit may include a disclosed compound and a second therapeutic agent for co-administration. The compound and second therapeutic agent may be provided as separate component parts. A kit may include a plurality of containers, each container holding one or more unit dose of the compound. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

The active compound is included in the pharmaceutically acceptable carrier in an amount sufficient to exert a therapeutically useful effect in the absence of undesirable side effects on the subject treated. A therapeutically effective concentration may be determined empirically by testing the compounds in known in vitro and in vivo model systems for the treated disorder. In some examples, a therapeutically effective amount of the compound is an amount that lessens or ameliorates at least one symptom of the disorder for which the compound is administered. Typically, the compositions are formulated for single dosage administration. The concentration of active compound in the drug composition will depend on absorption, inactivation, and excretion rates of the active compound, the dosage schedule, and amount administered as well as other factors known to those of skill in the art.

In some examples, about 1 mg to 2500 mg of a disclosed compound, a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s).

The disclosed compounds or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

When administered orally as a suspension, these compositions may be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the compound is typically provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

In certain embodiments the active compound disclosed herein may be stabilized with a cyclodextrin as described in U.S. Provisional Appl. 62/992,036, filed Mar. 19, 2020, which is incorporated herein by reference. In particular, in aqueous solutions cyclodextrins form inclusion complexes with the active compound through a process in which the water molecules located in the central cavity are replaced by either the whole active compound molecule, or by some lipophilic portion of the active compound structure. The stabilized active compound/cyclodextrin complex may be stored as a solid at a convenient temperature (e.g., −80 to 30° C., more particularly 4 to 22° C.) for desired period of time to then be re-dissolved using water to obtain a solution or a suspension to be used to administer the active compound. In certain embodiments, the stabilized active compound/cyclodextrin complex is in the form of a powder. In certain embodiments, the time period for the powder storage may be at least 360 days, more particularly at least 90 days and the time period for the powder storage may be at least 14 days, more particularly at least or 10 days Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil (e.g. sesame oil, olive, or pure oils like triolein). In addition, dosage unit forms can contain various other materials, which modify the physical form of the dosage unit, for example, coatings of sugar and other enteric agents.

The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily. In some examples, an oral dosage form is administered to the subject 1, 2, 3, 4, or more times daily. In additional examples, the compounds can be administered orally to humans in a dosage range of 1 to 1000 mg/kg body weight in single or divided doses. One illustrative dosage range is 0.1 to 40 mg/kg body weight orally (such as 0.5 to 20 mg/kg body weight orally) in single or divided doses. For oral administration, the compositions may be provided in the form of tablets containing about 1 to 2500 milligrams of the active ingredient, particularly 1, 5, 10, 15, 20, 25, 50, 75, 100, 150, 200, 250, 300, 400, 500, 600, 750, 800, 900, 1000, or 2500 milligrams of the active ingredient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- di- or triglycerides (e.g., triolein), and fatty acids, including oleic acid. Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The compounds can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The compounds can also be administered sublingually. When given sublingually, the compounds should be given one to four times daily in the amounts described above for IM administration.

The compounds can also be administered intranasally. When given by this route, the appropriate dosage forms are a nasal spray or dry powder. The dosage of the compounds for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds can be administered intrathecally. When given by this route, the appropriate dosage form can be a parenteral dosage form. The dosage of the compounds for intrathecal administration is the amount described above for IM administration.

The compounds can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used.

The compounds can be administered rectally by suppository. When administered by suppository, an illustrative therapeutically effective amount may range from about 0.5 mg to about 500 mg. When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

It should be apparent to one skilled in the art that the exact dosage and frequency of administration will depend on the particular compounds administered, the particular condition being treated, the severity of the condition being treated, the age, weight, general physical condition of the particular subject, and other medication the individual may be taking as is well known to administering physicians or other clinicians.

EXAMPLES

Materials and Methods

Antibodies and Reagents

Antibodies against p65 (#6956), Lamin A/C (#4777), GAPDH (#5174), β-actin (#4970, and #3700) were purchased from Cell Signaling Technology (CST, Danvers, MA). Fluor 488 and 594 conjugated secondary antibodies were from Jackson ImmunoResearch (West Grove, PA). For cell experiments, Ang II (#17150), PGE2 (#14010), ONO-AE3-208 (#14522), GW9662 (#70785) and oleic acid (#90260) were purchased from Cayman Chemical (Ann Arbor, MI). nLDL (#12-16-120412-TC) and oxLDL (#12-16120412-OX) were from Athens Research & Technology (Athens, Ga.). siPtger4 pool (M-048700-01-0005) and siControl pool2 (D-001206-14-05) were from Dharmacon (Lafayette, CO). RNAiMAX (#13778150) and Lipofectamine 2000 (#11668) were from Invitrogen (Waltham, MA). Human N-HA tagged FEM1A (#HG21487-NY) was purchased from Sino Biological (Beijing, China). pCMV4-p105 was from Addgene (plasmid #23288, Watertown, MA). $NO_2$—OA was synthesized, as previously described (Woodcock S R, Bonacci G, Gelhaus S L, Schopfer F J. Nitrated fatty acids: synthesis and measurement. Free Radic Biol Med. 2013; 59:14-16).

Cell Culture and Isolation of BMDMs

Murine RAW 264.7 cell line, 293T/17 cell line and Primary Umbilical Vein Endothelial Cells (PCS-100-010, HUVECs) were purchased from ATCC (Manassas, VA) and cultured in DMEM (Gibco) with 10% FBS (Thermo Fisher Scientific) or M199 (Gibco) supplemented with 20% FBS for HUVECs. BMDMs isolated from 12 to 16-week-old C57BL/6 wild type mice were cultured in bone marrow macrophage differentiation media. The differentiation medium was prepared by adding L-cell conditioned media (30%), non-essential amino acids (#11140-050, Gibco), sodium pyruvate (1 mM, #11360-070, Gibco), 2-Mercaptoethanol (55 μM) and 10% FBS into Iscove's Modified Dulbecco's Medium (IMDM, Gibco).

Animal Procedures

Ten weeks old male C57BL/6J mice were purchased from The Jackson Laboratory. The murine AAA model induced by AngII/PCSK9 gain-of-function mutation is well-established. After acclimation for 1 week, mice were fed a western diet (TD.88137, Envigo) and intraperitoneally injected with 2×1011 genomic copies of AAV-PCSK9.D377Y (AAV serotype 8, Penn Vector Core). Two weeks later, each mouse was subcutaneously implanted with two osmotic pumps (Model #2004, Alzet). One was loaded with AngII (#H-1706, Bachem), releasing at a rate of 1,500ng/kg/min, while the other one was loaded with PEG-400, OA or $NO_2$—OA at a delivery rate of 5 mg/kg/day for OA or $NO_2$—OA. After 4-weeks infusion, mice were euthanized and the maximal outer diameter of the suprarenal aorta was assessed with a digital caliper by a third person blinded to the treatment. Suprarenal aortas with a maximal diameter ≥50% larger than standard size (≥1.2 mm) were considered as abdominal aortic aneurysms. Mice dead within the first week of pump implantation or with a serum total cholesterol level less than 250 mg/dL were excluded from the study. All animal procedures were performed following the protocols approved by the Institutional Animal Care & Use Committee (IACUC) at the University of Michigan.

Total Cholesterol (TC) and Triglyceride Measurement

Serum total TC and TG levels were measured by enzymatic reaction (Wako Diagnostics, Osaka, Japan).

Histology Staining

H&E and Verhoeff Van Gieson staining of paraffin or frozen sections of mouse suprarenal abdominal aorta were performed by the In-Vivo Animal Core at the University of Michigan. Elastin degradation grade was calculated as we previously reported.

RNA Extraction and Quantification

Mice suprarenal aortas were collected after the measurement of their diameter. Human aortic aneurysm samples were obtained from the Department of Cardiac Surgery at the University of Michigan. Samples from humans and mice were snap-frozen in liquid nitrogen for later processing. RNA from tissue was extracted using TRIzol (#15596018, Invitrogen). RNA from cells was isolated with the RNeasy Mini Kit (#74106, QIAGEN). SuperScript™ III First-Strand Synthesis System (#18080051, Invitrogen) was used to reverse-transcribe mRNA into cDNA. Gene expression was quantified in triplicates by quantitative real-time PCR (qPCR) using IQ SYBR Green Supermix (#1708882, Bio-Rad) with the indicated gene primers.

Enzyme-Linked Immunosorbent Assay (ELISA)

MCP1, TNFα and IL6 levels in mouse plasma were measured by ELISA performed by the Cancer Center Immunology Core at the University of Michigan.

Fluorescence-Activated Cell Sorting (FACS)

The suprarenal aorta region from euthanized mice were completely perfused with PBS containing 2% of heparin. Tissues were digested using a cocktail of 450 U/mL collagenase type I (#17100-017, Gibco), 125 U/mL collagenase type XI (#C7657, Sigma-Aldrich), 60 U/mL hyaluronidase type I-s (#H3606, Sigma-Aldrich) and 60 U/mL DNase-I (#10104159001, Roche) at 37° C. for 90 minutes. Single cells filtered through a 70 μm cell strainer were blocked by Fc block (#14-0161-85, eBioscience) for 5 minutes on ice. After blocking, cells were incubated with fluorochrome-conjugated antibodies against CD45 (#48-0451, eBioscience), CD64 (#558455, BD), and CD11c (#47-0114, eBioscience) for 30 minutes on ice, washed, fixed with 2% PFA, and subjected to FACS analysis by the Flow Cytometry Core at the University of Michigan. Data were analyzed using FlowJo v10.6.1.

Boyden Chamber Transwell Migration Assay

HUVECs were seeded in the lower chambers of the Transwells (#CLS3464, Sigma-Aldrich) and cultured up to 80% confluence before treatment with or without AngII (100 nM) for 6 hours in OptiMEM I reduced serum medium (#31985-070, Gibco). RAW 264.7 cells starved with OptiMEM I overnight were seeded (2×105 per well) in the upper chambers of the transwells and treated with vehicle (ethanol), OA (2.5 μM) or $NO_2$—OA (2.5 μM) for additional 12 hours. Cells on the upper chamber were then removed by gently scraping with a cotton swab, and the membranes were fixed in 4% PFA for 15 min and stained with 0.1% crystal violet for 15 min at room temperature. Images were acquired by AMG Evos XI Core Imaging System. Quantification of the positively stained area was performed using Image J v1.52s.

Nuclear/cytoplasm protein extraction, co-Immunoprecipitation and immunoblotting NE-PER™ Nuclear and Cytoplasmic Extraction Reagents (#78835, ThermoFisher) were used for nuclear and cytoplasmic protein extraction. For Co-IP, cells were lysed using Cell Lysis Buffer (#9803, CST) supplemented with PMSF (#8553, CST), immunoprecipitated using Protein G Magnetic Beads (#7024, CST) and antibodies against HA (#AE008, ABclonal) or p50/p105 (#13586, CST) following the manufacture's protocol. For immunoblot, protein extracts were resolved in SDS-PAGE gels and transferred to nitrocellulose membranes. Membranes were blocked by 5% BSA and incubated with the primary antibody at 4° C. overnight followed by incubation with fluorescence conjugated secondary antibody for 1 h at room temperature. Band intensity was collected with the Odyssey® CLx Imaging System and quantified using Image Studio™ Lite.

EP4 receptor activity and cAMP Homogeneous Time-Resolved Fluorescence (HTRF) assay The effect of $NO_2$—OA on PGE2 induced EP4 activation was assessed using EP4 Receptor (human) Reporter Assay Kit (#601390, Cayman) in 293T/17 cells. Cells at 80% density were incubated on plates coated with transfection complex containing human EP4 receptors and a cAMP response element-regulated secreted alkaline phosphatase (SEAP) reporter. Activation of EP4 was quantified by adding a luminance-based alkaline phosphatase substrate and read in a chemiluminescence plate reader relative to the kit's standards. EP4 Inhibition assay was performed using cAMP-Gs HiRange kit (#62AM6PEB, Cisbio) following the manufacture's protocol and measured by Neo2 plate reader (BioTek, Winooski, Vt.). HTRF ratio (665/620) was converted to cAMP concentration using a cAMP standard.

Matrix Metallopeptidase (MMP) Zymography

Freshly differentiated BMDMs were cultured in the bone marrow macrophage-differentiation media until 80% confluence. Cells were starved for 24 h and incubated with PGE2 (500 nM) plus vehicle, OA (2.5 μM) or $NO_2$—OA (2.5 μM) for an additional 12 h. Then, the supernatant was collected and centrifuged to remove any residual debris. Measurement of MMP2 and MMP9 activity was performed by running the supernatant (using detergent-free loading buffer) in 1% gelatin gel, followed by staining with Coomassie blue.

In Silico Ligand-Receptor Docking Simulation

A modified crystal structure of the human EP4 receptor at 3.2 Å resolution has been determined. Protein-ligand docking simulation of $NO_2$—OA and EP4 was performed using an EADock DSS based online interface, SwissDock. Binding energies were determined using a CHARMM-based function.

Statistical Analysis

Statistical analysis was performed using GraphPad Prism 8.3.0 or R-3.6.2. Data were tested for normality using the Shapiro-Wilk test and tested for "normality vs. lognormality" when normalized over control. For data that passed the normality test, the residual plot was used to ensure the homogeneity of variance. Weighting was performed when necessary. ROUT with Q set at 1% was used to identify outliers for raw data. Unpaired Student t-test was used to compare the difference between two means, one-way ANOVA was used to compare means from more than two groups, and nonlinear regression or two-way ANOVA was used for data with two independent variables. Tukey's or Sidak post hoc test was added to compare individual means. For data that failed the normality test, the Mann-Whitney U test or Kruskal-Wallis test followed by Dunn's comparisons were used as an alternative. Mantel-Cox test was used for the survival assay. For non-linear regression, three or four parameters, global or separate fitting, and constraints were compared in Prism. For incidence analysis, 2×3 Fisher's exact test following the post hoc test was conducted in R using the "rcompanion" package. Tests were performed in two-tail except for supplementary FIG. 3A, in which treatment higher than control was chosen. Unless otherwise stated, continuous variables were all presented as mean±standard error of the mean (SEM). Results with $p<0.05$ for both the main test and the post hoc test were considered as statistically significant. All in vitro results were representative of at least three independent experiments.

Power Analysis

Power analysis was used to estimate the number of mice needed for the study based on the effect size and S/N ratio of a pilot study to achieve a power of 0.8 at $\alpha=0.05$ (https://www.stat.ubc.ca/~rollin/stats/ssize/n2.html)

Justification of Sex Factors

Samples from males and females were used in our studies to minimize the impact of sex differences. However, in the AngII- and hypercholesterolemia-induced AAA mouse model, we were limited to male mice because, in prior experiments, less than 10 percent of female mice developed AAA with this model (data not shown).

Results

Nitro-oleic acid attenuates AAA formation in the mouse model

Figure 1A:
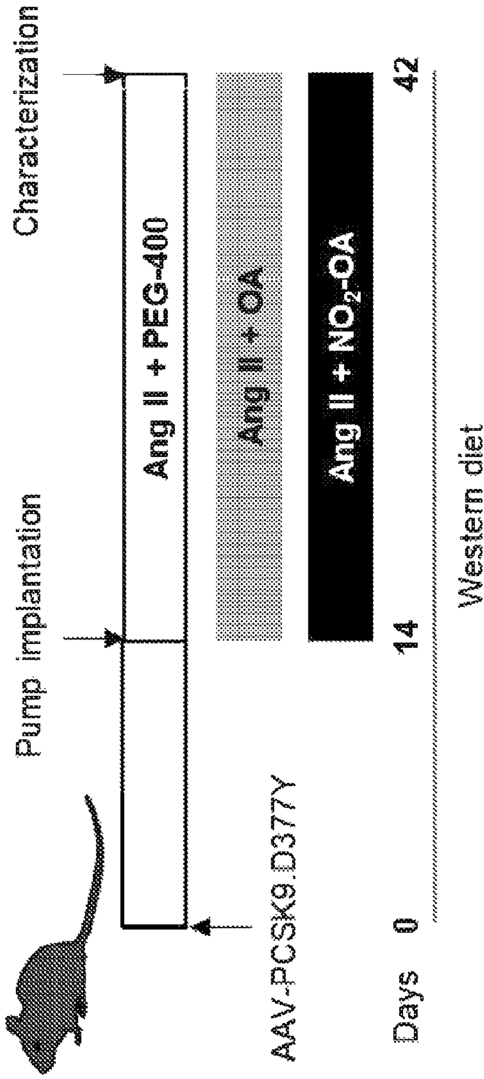
Figure 1C:
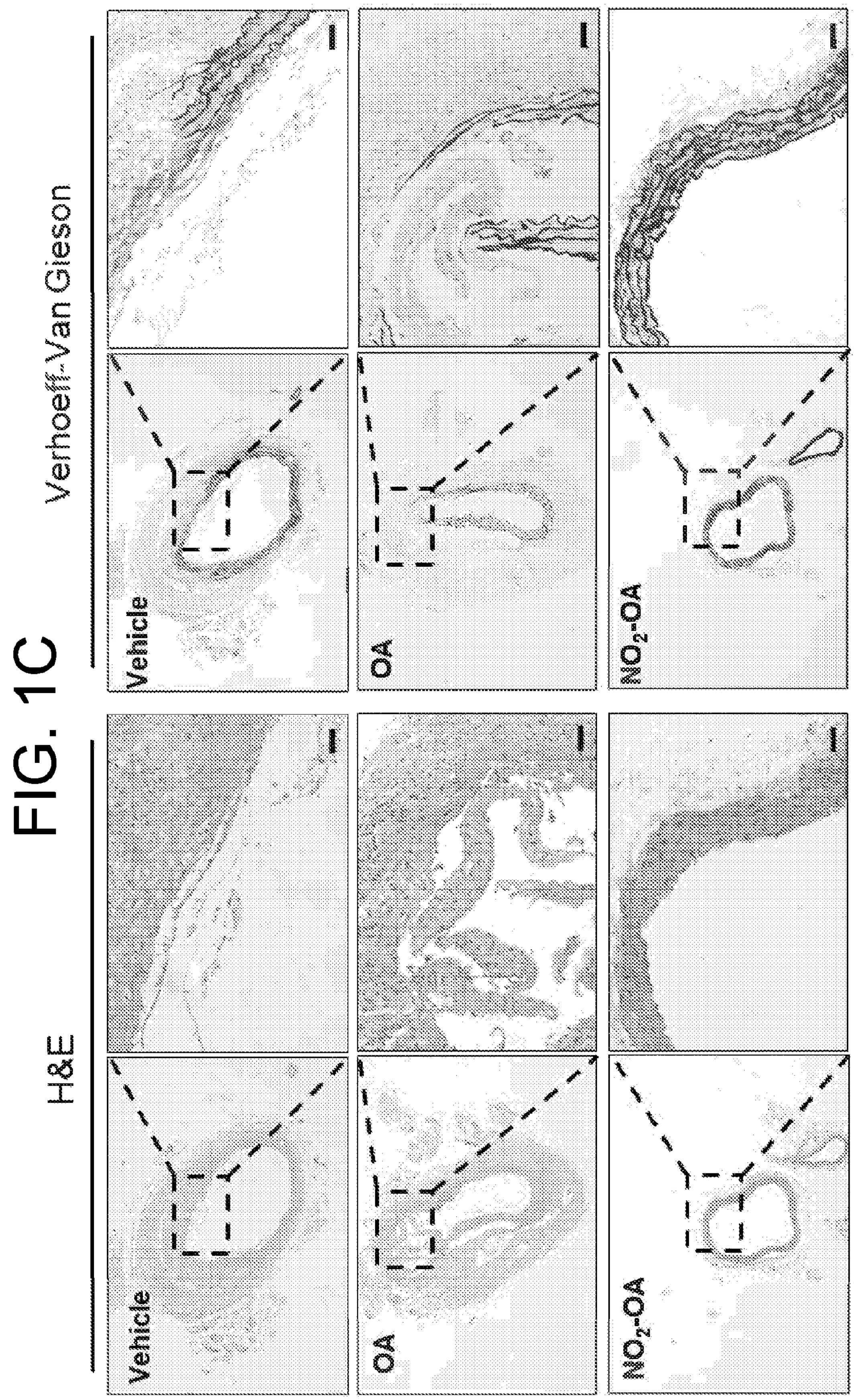
Figure 1D:
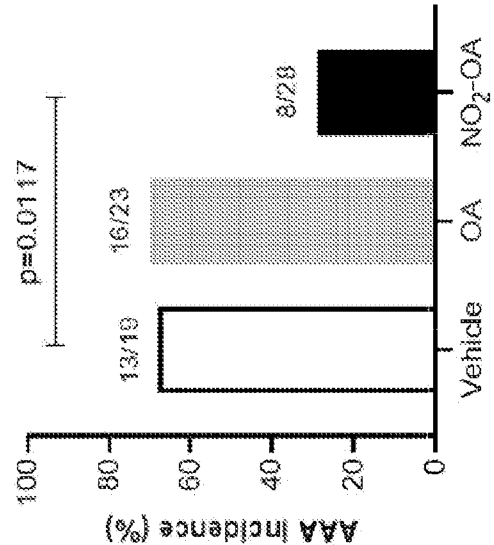
Figure 1E:
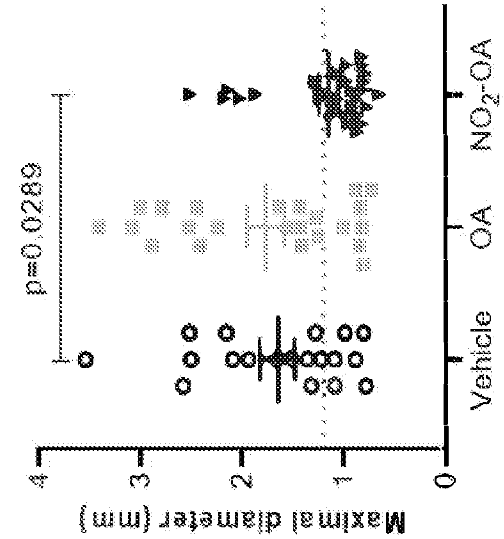
Figure 1F:
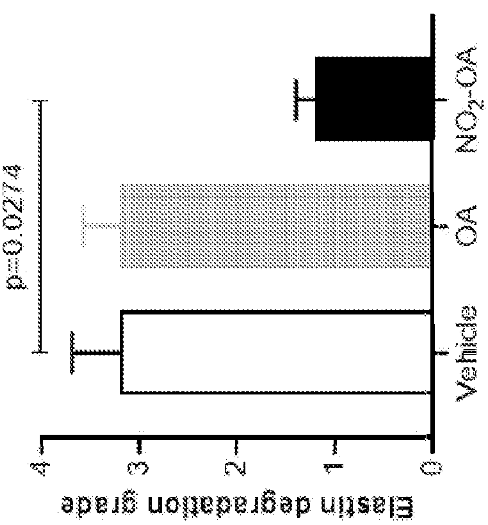

We first tested whether $NG_2$-OA could protect against AAA development in an Ang II plus hypercholesterolemia model of AAA in C57BL/6 wild type mice. Three groups of mice (n=25 to 30 per group) received a chronic subcutaneous infusion of either vehicle control (PEG-400), OA, or $NG_2$-OA, (FIG. 1A). After 4-weeks, a significant decrease in AAA incidence was observed in $NG_2$-OA treated mice when compared to vehicle (28.6% vs. 68.4%, p=0.0117) or OA (28.6% vs. 69.6%, p=0.0078) treated group (FIG. 1B, C). This effect was accompanied by a significant decrease in the maximal diameter of the suprarenal aorta region in the $NG_2$-OA treated group when compared to the vehicle (1.16±0.09 mm vs. 1.65±0.17 mm, p=0.0289) or OA (1.16±0.09 mm vs. 1.78±0.18 mm, p=0.0121) treatment groups (FIG. 1D). While ECM degradation is prominent in the vehicle control and OA-treated mice, $NG_2$-OA-treatment was protective, maintaining vascular integrity and significantly reduced elastin fiber degradation (p=0.0274 vs. vehicle and p=0.0304 vs. OA, FIG. 1E, F). Metabolic changes did not account for the $NG_2$-OA protective effect as no changes in cholesterol or body weight were observed. While $NG_2$-OA significantly decreased the serum TG levels when compared to vehicle (p=0.0048), this decrease was not specific as TG levels in OA-treated mice were significantly lower than the vehicle (p=0.0136), and no significant difference in serum TG levels was observed between the $NG_2$-OA and OA groups. Overall, these results show specific protection by $NO_2$—OA against AAA development in vivo, an effect that is not shared by OA.

Nitro-Oleic Acid Prevents Leukocyte/Macrophage Infiltration in the Vasculature

Figure 2B:
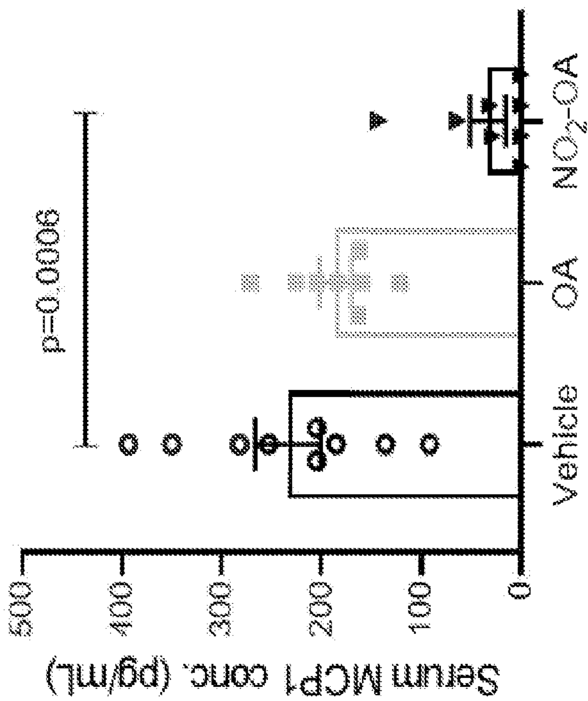
FIG. 2. $NO_2$—OA treatment suppressed leukocytes/macrophages infiltration in the vasculature. (A) Quantification of gene expression levels in the mice suprarenal aorta region by real-time PCR (n=3 to 4). (B, C) Serum cytokines levels measured by ELISA (n=8 to 11). (D) FACS of single cells isolated from the mice suprarenal aorta region. Each sample is the pool of cells from three mice (n=3). (E, F) Quantification of the percentage of CD45+ leukocytes and CD64+, CD11c+M1-like macrophages in total cells from the FACS analysis. Ordinary one-way ANOVA followed by Tukey's test was performed for (A), (E) and (F). For ELISA in (B) and (C), to avoid the effect of the non-detected data point, a non-parametric Kruskal-Wallis test followed by Dunn's multiple comparisons was performed by adding zero to the missing data point. Data presented as mean±SEM. A $p<0.05$ for both the main test and post hoc test was considered statistically significant.
Figure 2A:
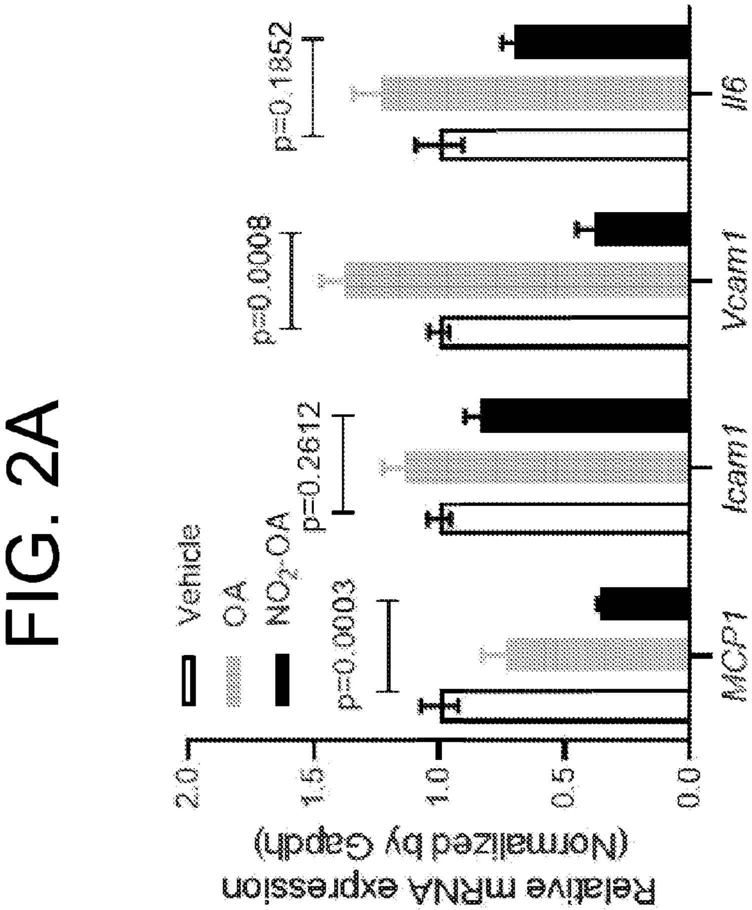
Figure 2C:
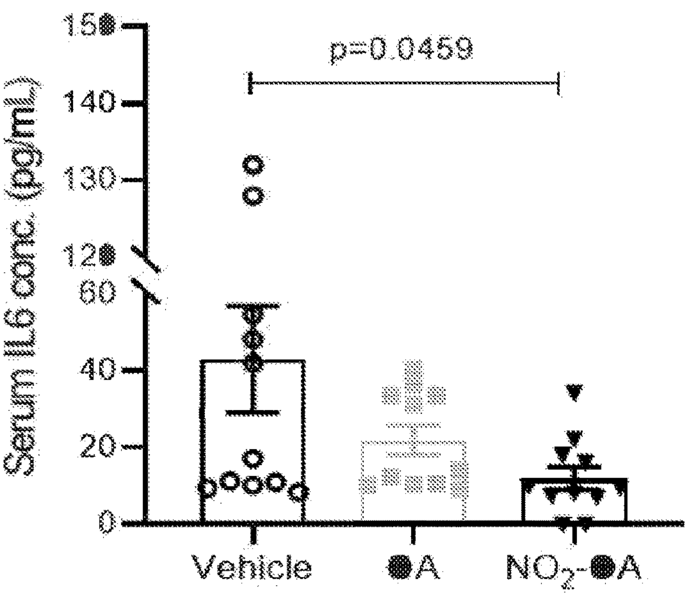
Figure 2D:
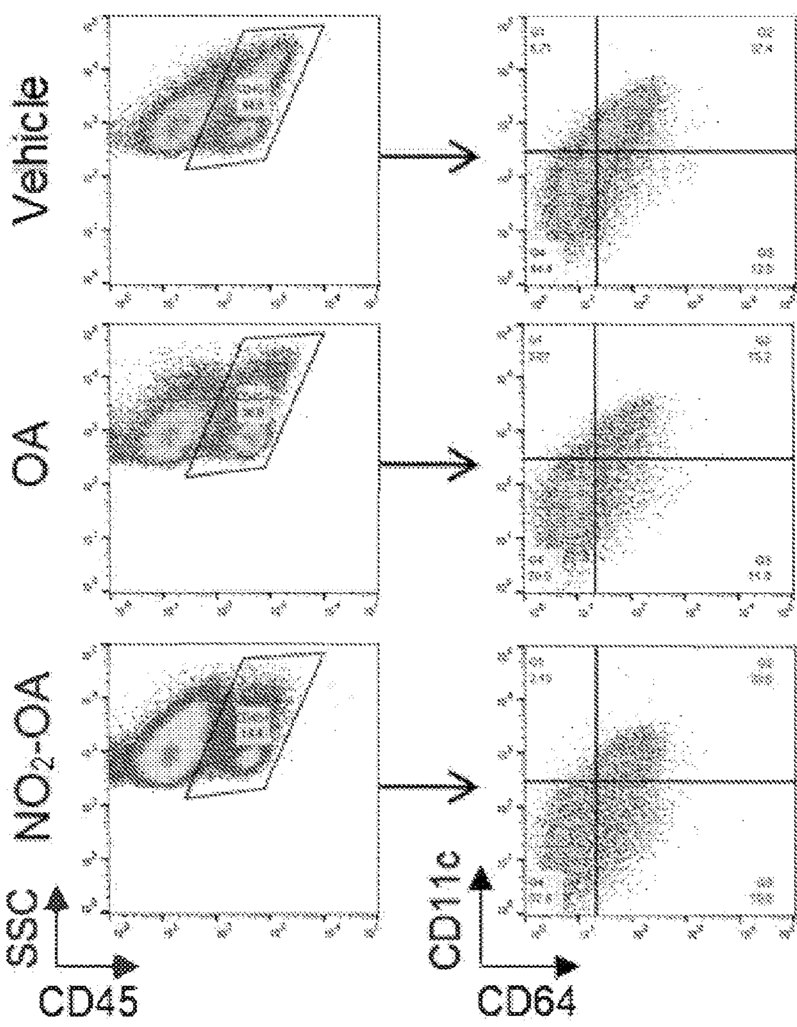
Figure 2E:
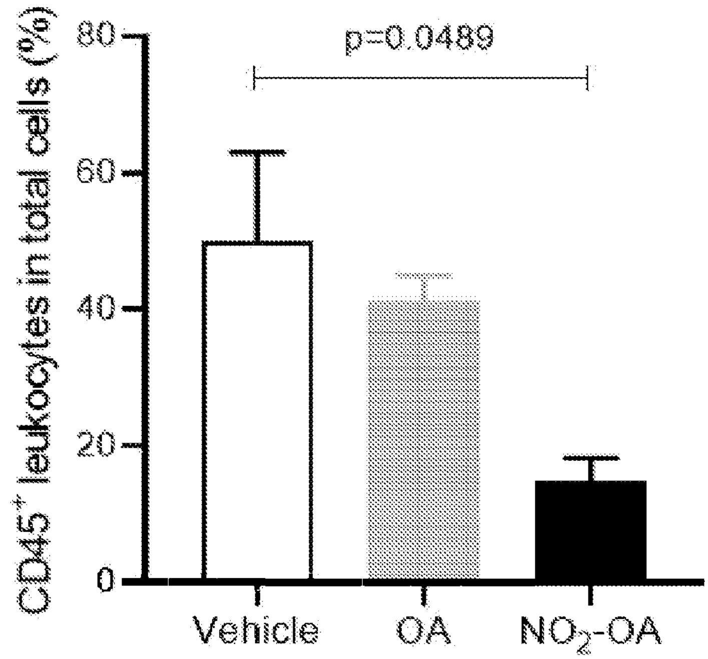
Figure 2F:
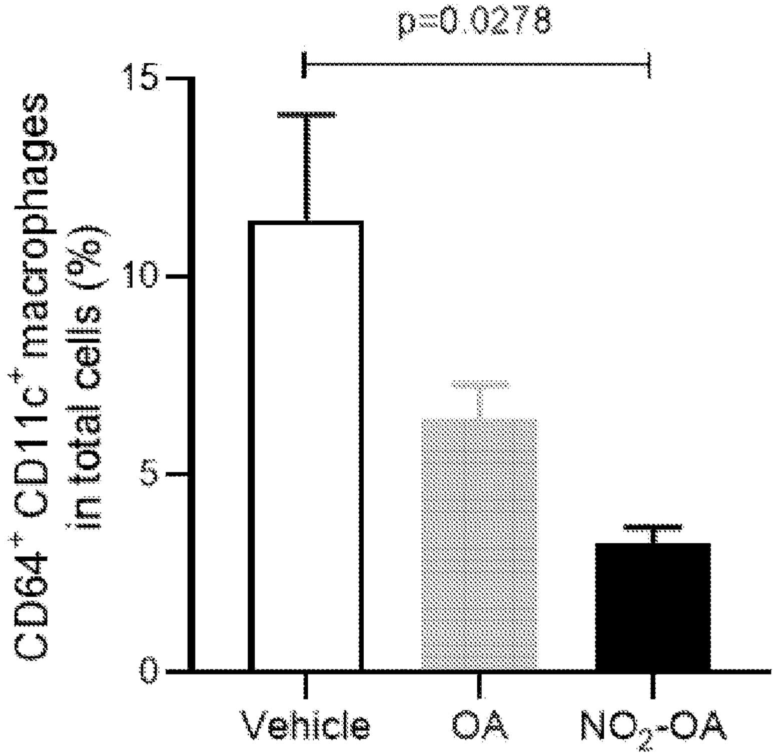

The contribution of infiltrated leukocytes/macrophages in the vasculature to AAA development has long been demonstrated. Hence, we tested the effect of $NO_2$—OA treatment on the infiltration process in vivo by evaluating the expression of several genes related to monocyte/endothelial cell-cell interaction. Mice treated with $NO_2$—OA had significantly decreased expression of the vascular cell adhesion protein 1 (Vcam1, p=0.0008) and MCP1 genes (p=0.0003, FIG. 2A) when compared with the vehicle control group. The expression of intercellular adhesion molecule 1 (Icam1) in the $NO_2$—OA group, however, was not statistically significant (p=0.2698 vs. vehicle, FIG. 2A). These local responses were also observed systemically, where protein levels of both circulating MCP1 (p=0.0006) and IL6 (p=0.0459) were significantly decreased by $NO_2$—OA (FIG. 2B, C). In order to evaluate the role of infiltrating leukocytes and macrophages in the inflammatory responses, the suprarenal aorta was digested into single cells, and the number of leukocytes (CD45+) and M1 like macrophages (CD64+, CD11c+) were counted (FIG. 2D). Compared with the vehicle group, significantly fewer leucocytes (CD45+) appeared in the vasculature upon $NO_2$—OA treatment (14.87±3.28% vs. 50.03±13.02% in vehicle control, p=0.0489, FIG. 2E). Notably, the abundance of pro-inflammatory M1 like macrophages (CD64+, CD11c+) was also decreased in the NO2-OA group (3.27±0.42% vs. 11.43±2.65% in vehicle control, p=0.0338, FIG. 2F), which is consistent with the previous observation that Nitro-FAs affect the differentiation, adhesion and polarization of macrophages. Additionally, we treated HUVECs with Ang II for 6 h and used the conditioned medium to induce migration of RAW 264.7 cells. We observed that $NO_2$—OA significantly inhibits endothelial-dependent macrophage migration in the presence of Ang II but not under basal conditions. These data indicate that $NO_2$-OA is effective in limiting endothelial-dependent leukocyte/macrophage migration to the AAA lesion area.

Nitro-Oleic Acid Inhibits Ox-LDL Induced NFκB Activation and Pro-Inflammatory Responses in Part Via Activation of PPARγ

Figures 3A, 3B, 3C:
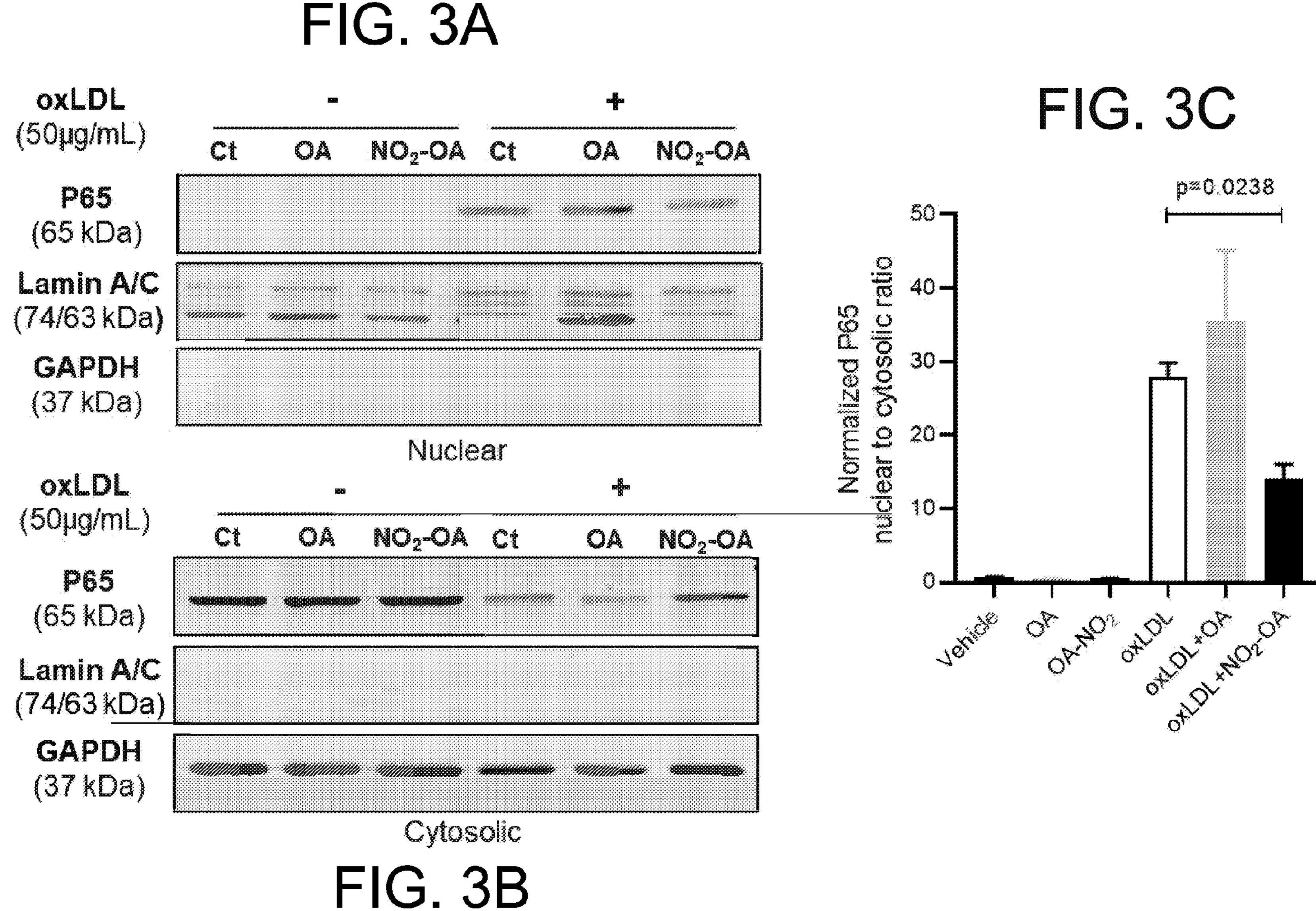
FIG. 3. $NO_2$—OA prevents oxLDL-induced NFκB activation and pro-inflammatory cytokine production. Primary BMDMs were pretreated with vehicle, OA (2.5 μM) or $NO_2$—OA (2.5 μM) for 1 h, followed by treatment of oxLDL (50 to 100 μg/ml) for the indicated times. (A, B) Nuclear (A) and cytoplasmic protein (B) fractions were isolated 1 h after oxLDL treatment and subjected to western blot with antibodies against p65, lamin a/c (nuclear marker) and GAPDH (cytosolic marker). Representative western blot images of three independent experiments are shown. (C) Quantification of the p65 nuclear to cytoplasmic ratio by image studio (normalized by the internal control, n=3). (D-F) Following 8 h of oxLDL treatment, levels of IL6, MCP1 and TNFα in the cell medium were measured by ELISA (n=4). (G) Real-time PCR quantification of gene expression levels of IL1b and Mmp9 in total mRNA extracted from the BMDMs. (C) Ordinary one-way ANOVA followed by Tukey's test was performed. As of (D-F), the basal level contains several non-detectable values, so ordinary one-way ANOVA followed by correction of FDR were performed for the oxLDL-treated groups only. Ordinary one-way ANOVA followed by Tukey's test was performed for (G). Data presented as mean±SEM. A $p<0.05$ for both the main test and post hoc test was considered statistically significant.
Figure 3G:
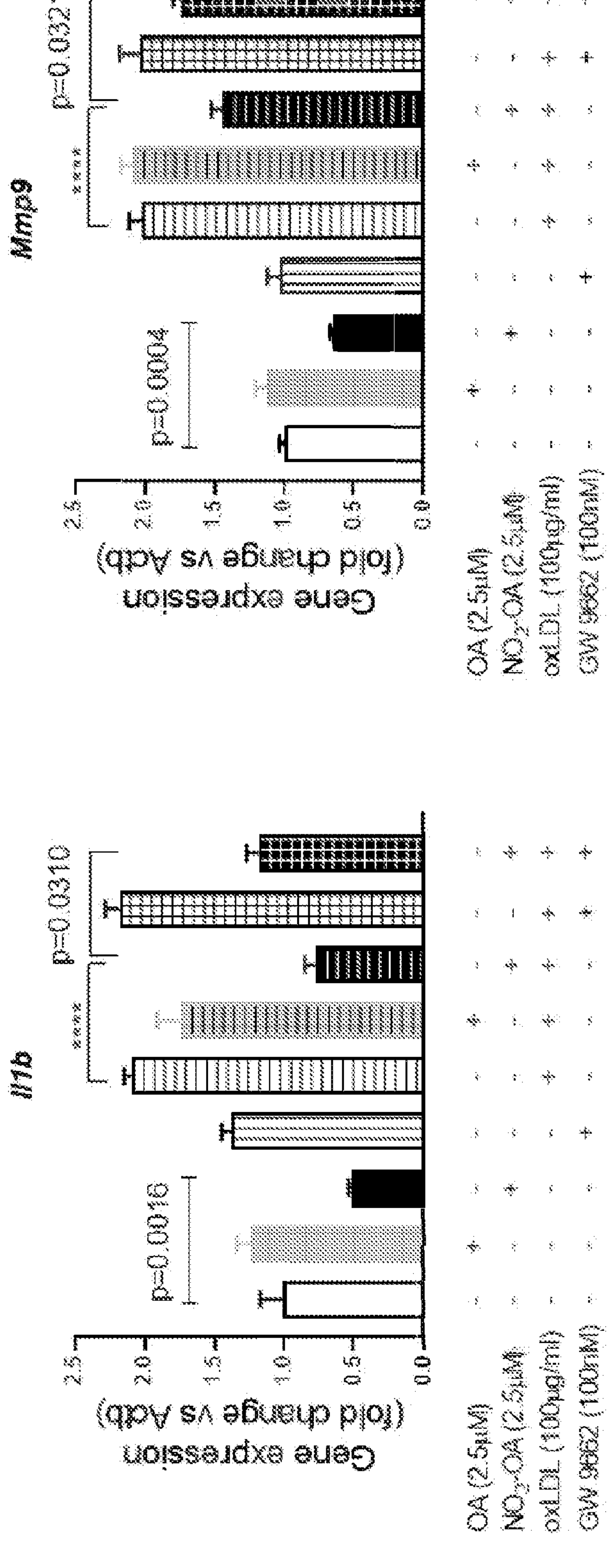

While the role of oxLDL in the initiation and development of atherosclerosis is well established, a recent study utilizing a systematic approach suggested that oxLDL also participates in the formation and development of AAA via activation of inflammatory responses. Thus, we hypothesized that $NO_2$—OA exerts a protective role through the inhibition of the oxLDL-induced macrophage inflammatory activation. Here, BMDMs were treated with oxLDL (50 μg/ml), and oxLDL-induced p65 nuclear translocation was evaluated in nuclear and cytoplasmic fractions (FIG. 3A, B). We found that $NO_2$—OA significantly inhibited oxLDL-induced p65 nuclear translocation, with a nuclear to cytoplasmic ratio of 14.10±1.92 vs. 27.93±1.89 in the control group (p=0.0238, FIG. 3C). Further analysis of inflammatory cytokines in oxLDL-treated cell medium showed a significant decrease in IL6 level (p=0.0327 vs. control) and a marginally significant reduction in MCP1 level (p=0.0664 vs. control). However, no significant difference was observed in TNFα levels, as compared to the control group (p=0.3290, FIG. 3D-F. PPARγ expression in monocytes/macrophages is upregulated by oxLDL, which may amplify its role under disease conditions like those predisposing for atherogenesis and AAA development. We showed that oxLDL-induced expression of the pro-inflammatory genes Il1b, and Mmp9, which are responsible for ECM degradation, were significantly decreased by $NO_2$—OA treatment (p<0.0001 vs. control), and that the protective effect of $NO_2$—OA was partially blocked by giving an irreversible PPARγ antagonist, GW9662 (p=0.0310 for Il1b, and p=0.0321 for Mmp9, FIG. 3G) or siPPARγ, indicating that PPARγ signaling is partially responsible for the protective effect of $NO_2$—OA on oxLDL-induced pro-inflammatory responses.

Nitro-Oleic Acid is a Biased Regulator of PGE2-Dependent EP4 Signaling

Figure 4C:
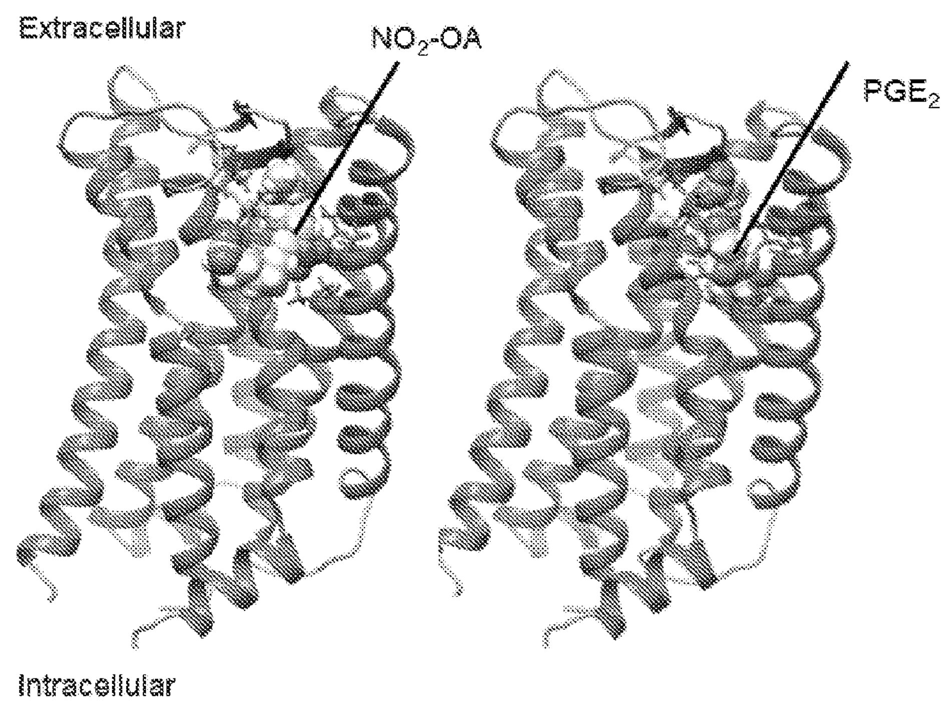
Figure 4D:
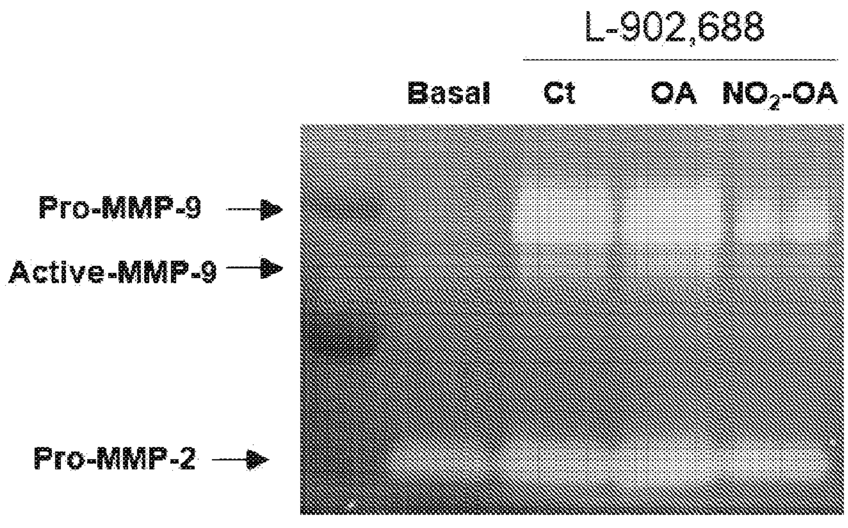

To address other pathways potentially contributing to the N02-OA protective effects, we investigated the PGE2-dependent EP4 signaling. It has been reported that a signaling axis involving the macrophage cyclooxygenase 2 (COX2), the microsomal isoform of prostaglandin E synthase 1 (mPGES1) and EP4 contributes to AAA development. For example, COX2, mPGES-1, and EP4 levels are upregulated at human aneurysm lesion sites. Similar upregulation was also seen in human thoracic aneurysm lesions, and the suprarenal aorta region of the AngII plus hypercholesterolemia induced murine AAA model. EP4 receptors are highly expressed in macrophages and are responsible for PGE2-dependent upregulation of MMP secretion. By overexpressing EP4 in 293T cells, we demonstrated that $NO_2$—OA significantly rightward shifted the dose-response curve over a range of concentrations of the EP4 agonist PGE2, with a best-fit EC50 of 1.2 nM vs.109.5 μM in the control group (p=0.0069, FIG. 4A). Moreover, $NO_2$—OA dose-dependently reduced PGE2-induced (IC90 10 nM) recruitment of cAMP to the EP4 Gs-coupled receptor with a best-fit IC50 at 2.8 μM (R2=0.9142, FIG. 4B). Molecular-receptor docking results showed that the predicted binding site of $NO_2$—OA with the highest score is close to the orthosteric binding pocket for PGE2 (FIG. 4C). MMPs, especially MMP2/9, play essential roles in ECM degradation and AAA development. We then used gelatin zymography to determine the activity of macrophage MMP2/9 upon $NO_2$—OA treatment. In BMDMs, PGE2 upregulates MMP9 expression, and this effect can be significantly diminished by $NO_2$—OA treatment, while no significant changes were observed for MMP2 activity (FIG. 4D). Aside from its positive contribution to ECM degradation, the PGE2-dependent activation of the EP4 receptor exerts anti-inflammatory actions by recruiting EPRAP, which inhibits NFκB and MEK activation through binding to p105 and preventing its phosphorylation. Herein, our results demonstrated that $NO_2$—OA does not suppress the PGE2-mediated protective effect against LPS-induced macrophage activation, as reflected by the expression of Tnf, Il6, and Ccl4. Moreover, Co-IP assay in cells overexpressing HA-tagged EPRAP (FEM1A), and p105 showed that up to 5 μM of $NO_2$—OA had no significant effect on the ERRAP/P105 interaction. Overall, these results indicate that $NO_2$—OA serves as a biased regulator of EP4-dependent PGE2 signaling.

In view of the many possible embodiments to which the principles of the disclosed invention may be applied, it should be recognized that the illustrated embodiments are only preferred examples and should not be taken as limiting the scope of the invention.

What is claimed is:

1. A method of treating an aneurysm, comprising administering to a subject a therapeutically effective amount of 10-nitro-octadec-9-enoic acid.

2. The method of claim 1, wherein the aneurysm is an aortic aneurysm.

3. The method of claim 1, wherein the aneurysm is a vascular aneurysm.

4. The method of claim 2, wherein the aortic aneurysm is an abdominal aortic aneurysm.

5. The method of claim 2, wherein the aortic aneurysm is a thoracic aortic aneurysm or a thoracoabdominal aortic aneurysm.

6. The method of claim 1, wherein the aneurysm is an intracranial aneurysm.

7. The method of claim 1, wherein the aneurysm is an aneurysm of celiac artery, mesenteric artery, renal arteries, splenic artery, hepatic artery, iliac arteries, femoral artery, popliteal artery or any branch of the aorta.

* * * * *